(12) United States Patent
Winkler et al.

(10) Patent No.: US 6,451,785 B1
(45) Date of Patent: Sep. 17, 2002

(54) BETA LACTAMS AS ANTIPROLIFERATIVE AGENTS

(75) Inventors: James David Winkler, Fort Washington, PA (US); Floyd Harold Chilton, III, Pilot Mountain, NC (US)

(73) Assignees: SmithKline Beecham Corporation, Philadelphia, PA (US); Wake Forest University, Winston-Salem, NC (US)

( * ) Notice: Subject to any disclaimer, the term of this patent is extended or adjusted under 35 U.S.C. 154(b) by 0 days.

(21) Appl. No.: 09/423,420

(22) PCT Filed: May 8, 1998

(86) PCT No.: PCT/US98/09481

§ 371 (c)(1),
(2), (4) Date: Jan. 28, 2000

(87) PCT Pub. No.: WO98/49897

PCT Pub. Date: Nov. 12, 1998

Related U.S. Application Data

(60) Provisional application No. 60/044,382, filed on May 9, 1997.

(51) Int. Cl.[7] .............................................. A61K 31/395
(52) U.S. Cl. ................................................. 514/210.02
(58) Field of Search ..................................... 514/210.02

(56) References Cited

U.S. PATENT DOCUMENTS 3,951,951 A    4/1976  Smale ......................... 260/239

*Primary Examiner*—James H. Reamer
(74) *Attorney, Agent, or Firm*—Dara L. Dinner; Stephen Venetianer; Charles M. Kinzig

(57) ABSTRACT

A method of inhibiting or reducing cell proliferation in a human or mammal is disclosed. This method involves administering to a human or mammal an effective amount of CoA-independent transacylase inhibiting amount of a compound of the formula disclosed in the specification.

28 Claims, 7 Drawing Sheets

Effect of CoA-IT Inhibitors on DNA Ladder Formation in Murine P388 Leukemia Cells.

Effect of CoA-IT Inhibitors on DNA Ladder Formation in Human Acute Myelogenous Leukemia Cells.

BETA LACTAMS AS ANTIPROLIFERATIVE AGENTS

This application is a 371 of PCT/U.S.98/09481 filed May 8, 1998, wherin claims benefit of Ser. No. 60/044,382 filed May 9, 1997.

FIELD OF THE INVENTION

This invention relates to novel compounds, pharmaceutical compositions thereof, and their use as anti-inflammatory agents and for the treatment of cell proliferation and cancer in mammals.

BACKGROUND OF THE INVENTION

Over the past three decades, it has been firmly established that the in vivo modulation of levels of the polyunsaturated fatty acid, arachidonic acid (AA) and oxygenated metabolites of arachidonic acid is intimately linked to human disease. Our laboratories have focused on the pathways and enzyme activities that acylate AA into membrane phospholipid of inflammatory and neoplastic cells (for a review, see Chilton et al., Biochim. Biophys. Acta 1299: 1–15 (1996)). These studies indicate that there are as many as 20 different arachidonate-containing phospholipid molecular species in any given inflammatory or neoplastic cell type. We have demonstrated that AA moves through different AA-containing phospholipid molecular species in a sequential fashion requiring several different enzyme activities (FIG. 1). Initially AA is converted to AA-CoA by fatty acyl CoA synthase(s). There appears to be specific fatty acyl CoA synthase(s) which utilize AA but not other fatty acids. Once formed, arachidonoyl-CoA may be incorporated into 1-acyl-2-lyso-sn-glycero-3-phosphocholine by CoA-dependent acyl transferase(s). This AA in 1-acyl-2-AA-sn-glycero-3-phosphocholine is then transferred to 1-ether-linked phospholipids such as 1-alkyl-2-AA-sn-glycero-3-phosphocholine and 1-alk-1-enyl-2-AA-sn-glycero-phosphoethanolamine. 1-Ether-linked phospholipids contain the bulk of AA found in most inflammatory and neoplastic cells. This latter reaction is orchestrated by the action of the enzyme CoA-independent transacylase (CoA-IT).

Coenzyme A-independent transacylase (CoA-IT) is an enzyme responsible for the movement of arachidonate between phospholipid molecular species of inflammatory cells. CoA-IT removes arachidonate from the sn-2 position of 1-acyl-containing phospholipids, such as 1-acyl-2-arachidonoyl-sn-glycero-3-phosphocholine (1-acyl-2-arachidonoyl-GPC). It then transfers that arachidonate to a suitable lyso-phospholipid acceptor, such as 1-alkyl-2-lyso-GPC and 1-alkenyl-2-lyso-sn-glycero-3-phosphoethanolamine (Sugiura et al., J. Biol. Chem. 262: 1199–1205 (1987); Kramer and Deykin, Biol. Chem. 258: 13806–13811 (1983); Chilton et al., J. Biol. Chem. 258: 7268–7271 (1983)). This activity is selective for 20 carbon fatty acyl groups and is the mechanism by which inflammatory cells move arachidonate into specific phospholipid pools prior to its release (Winkler and Chilton, Drug News Perspec. 6: 133–138 (1993); Snyder et al., J. Lipid Mediat. 10: 25–31 (1994)).

Although the pathway for the incorporation and remodeling of AA among phospholipids have been worked out within inflammatory cells and neoplastic cells, we have only recently begun to understand the functional significance of this pathway. We have recently discovered structurally distinct families of molecules (characterized by SK&F 45905 (2-[2-[3-(4-Chloro-3-trifluoromethylphneyl)ureido]-4-tifluromethylphenoxy]-4,5-dichlorobenzene sulfonic acid) and SK&F 98625 (Diethyl 7-(3,4,5-triphenyl-2-oxo-2,3-dihydroimidazol-1yl)heptane phosphonate)) which are capable of inhibiting CoA-IT (Chilton et al., Biochemistry 34: 5403–5410 (1995); Winkler et al., J. Pharmacol. Exp. Ther. 274: 1338–1347 (1995)). When provided acutely or chronically to inflammatory or neoplastic cells, these inhibitors attenuate the movement labeled AA from 1-acyl-linked phospholipids to 1-alkyl- and 1-alkenyl-linked phospholipids (Chilton et al., Biochemistry 34: 5403–5410 (1995)). In addition to SK&F 45905 and SK&F 98625, it has been established that the antineoplastic agent1-0-octadecyl-2-0-methyl-phosphocholine (ET-18-0-$CH_3$) is also a potent inhibitor of the enzyme CoA-IT (Winkler et al., J. Pharmacol. Exp. Ther. 279: 956–966 (1996)). Moreover, other studies revealed that the CoA-IT inhibitors SK&F 45905 and SK&F 98625 possess antiproliferative properties (Surette et al., Biochemistry 35: 9187–9196 (1996); Winkler et al., J. Pharmacol. Exp. Ther. 279: 956–966 (1996)). More specifically, all CoA-IT inhibitors, including ET-18-0-$CH_3$, attenuate cell proliferation and induce apoptosis in several neoplastic cell lines. Structurally related compounds which possess no inhibitory activity toward CoA-IT do not induce apoptosis. In addition, inhibitors of phospholipase $A_2$, 5-lipoxygenase, and cyclooxygenase do not induce apoptosis suggesting that free AA or its metabolites are not responsible for this process. The aforementioned discoveries indicate that blockage of the enzyme CoA-IT is a novel chemotherapeutic approach for the treatment of proliferative disorders such as cancer.

There exists a need to find other CoA-IT inhibitors with better in vivo pharmacological and toxicological profiles. These compounds should block cell proliferation of diseased cells and hence provide potential treatment for cancers, such as leukemia and other proliferative diseases and conditions such as psoriasis.

SUMMARY OF THE INVENTION

The present invention is a method to decreasing, inhibiting or reducing disease or disorders of cell proliferation in a mammal, and inducing apoptosis in a mammal, preferably in a human, by inhibition of the enzyme CoA-IT. Therefore the present invention is to the use of an effective amount of a CoA-IT inhibitor of Formula (I) for the treatment of said cell proliferation, in mammals, preferably humans, in need of such treatment, by administering to said human an effective amount of a CoA-IT inhibitory compound, or pharmaceutically acceptable salt thereof. A preferred disease state, for treatment associated with cell proliferation, is psoriasis, rheumatoid arthritis or atherosclerosis.

Another aspect of the present invention is to a method of treating a cancerous cell growth in a mammal, preferably a human, in need of such treatment, which method comprises administering to said mammal an effective amount of a compound of Formula (I). A preferred disease state for treatment associated with cancerous cell growth is leukemia.

Another aspect of the present invention is to a method of inducing apoptosis in a mammal, in need of such treatment which method comprises administering to said human or mammal an effective amount of a CoA-independent transacylase (CoA-IT) inhibitor, of Formula (I).

DETAILED DESCRIPTION OF THE INVENTION

Figure 1:
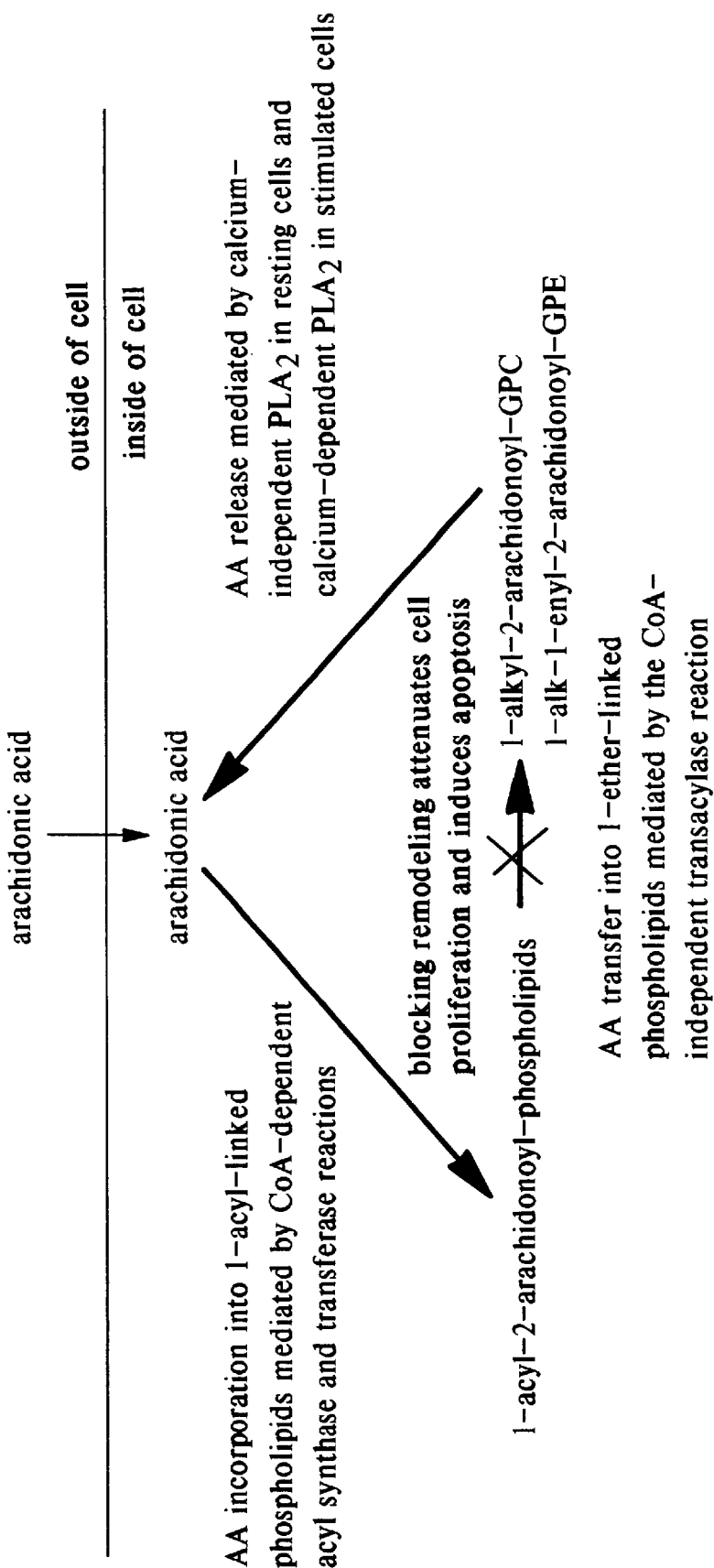
FIG. 1 is a scheme of the movement of arachidonic acid that occurs and this relationship to apoptosis.

Inhibition of CoA-IT activity results in a decrease in cell growth and proliferation, in induction of apoptosis, thereby providing therapeutic utility in proliferative and cancerous disorders. The present invention therefore provides a method for treating proliferative and cancerous disorders by CoA-IT inhibition. This inhibition is by administering to a mammal, in need of such treatment an effective amount of a compound according to Formula (I). This inhibition will result in the treatment, and potential prophylaxis, of proliferative occurrences in mammals, preferably humans. Such proliferative states in mammals may include, but are not limited to, diseases (such as cancers), dermatological diseases (such as psoriasis) and inflammatory diseases (such as, rheumatoid arthritis). Treatment of both acute and chronic diseases are thereby possible. For the purposes herein, the compounds of Formula (I) are preferential and selective inhibitors of CoA-IT.

Compounds of Formula (I) are represented by the structure:

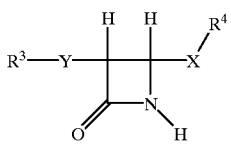

wherein

Y is NH;

X is O or S(O)m;

m is 0 or an integer having a value of 1, or 2;

$R_3$ is optionally substituted triphenylmethyl;

$R_4$ is optionally substituted $C_{1-10}$ alkyl, $(CR_{10}R_{20})n$—C≡C—$R_5$, or $(CR_{10}R_{20})_nC(R_{10})$=$C(R_7)_2$;

n is an integer having a value of 1 to 4;

$R_{10}$ and $R_{20}$ are independently hydrogen or $C_{1-4}$ alkyl;

$R_5$ is hydrogen, alkyl, aryl, arylalkyl, heteroaryl, heteroarylalkyl, $C(O)_2R_6$, or $C(O)R_6$ wherein the alkyl, aryl, arylalkyl, heteroaryl, and heteroarylalkyl moieties may be optionally substituted;

$R_6$ is $C_{1-10}$ alkyl, aryl, arylalkyl, heteroaryl, heteroarylalkyl, heterocyclic, or heterocyclicalkyl moiety, wherein the alkyl, aryl, arylalkyl, heteroaryl, heteroarylalkyl, heterocyclic, or heterocyclicalkyl moieties may be optionally substituted;

$R_7$ is independently hydrogen, $C_{1-10}$ alkyl, aryl, arylalkyl, heteroaryl, heteroarylalkyl, heterocyclic, or heterocyclicalkyl, wherein the alkyl, aryl, arylalkyl, heteroaryl, heteroarylalkyl, heterocyclic, or heterocyclicalkyl moieties may be optionally substituted;

or a pharmaceutically acceptable salt thereof.

Suitably, X is O or S(O)m; and m is 0 or an integer having a value of 1or 2. Preferably m is 0 or 2.

Suitably, $R_3$ is optionally substituted triphenylmethyl group. The phenyl rings may be independently substituted one to three times by halogen, such as fluorine, chlorine, bromine or iodine; hydroxy; hydroxy substituted $C_{1-10}$ alkyl; $C_{1-10}$ alkoxy, such as methoxy or ethoxy; halosubstituted $C_{1-10}$ alkoxy; S(O)m alkyl, such as methyl thio, methylsulfinyl or methyl sulfonyl; S(O)m aryl; amino, mono & di-$C_{1-10}$ alkyl substituted amino; $C_{1-10}$ alkyl; halosubstituted $C_{1-10}$ alkyl, such as $CF_3$; CHO, C(O)$C_{1-10}$ alkyl, C(O)aryl, $C(O)_2R_8$, wherein R8 is $C_{1-10}$ alkyl, aryl, or arylalkyl; $C(O)NR_9R_{11}$; cyano; $S(O)_2NR_9R_{11}$; $N(R_{10})C(O)R_6$; $N(R_{10})C(O)NR_9R_{11}$; $N(R_{10})C(O)OR_6$; or $N(R_{10})S(O)_2R_6$.

Suitably, $R_4$ is optionally substituted $C_{1-10}$ alkyl, $(CR_{10}R_{20})n$—C≡C—$R_5$, $(CR_{10}R_{20})_nC(R_{10})$=$C(R_7)_2$; wherein n is an integer having a value of 1to 4. Preferably n is 1.

When $R_4$ is an optionally substituted $C_{1-10}$ alkyl, the alkyl moiety may be straight or branched, and may be substituted one or more times, independently by halogen, such as fluorine; hydroxy; $C_{1-10}$ alkoxy; S(O)m alkyl, wherein m is 0, 1 or 2; amino, mono & di-substituted amino, such as $NR_9R_{11}$ group; wherein $R_9$ and $R_{11}$ are as defined below or $R_9$ and $R_{11}$ together with the nitrogen to which they are attached cyclize to form a 5 to 7 membered ring which optionally includes an additional heteroatom selected from O/N/S; —O$(CR_{10}R_{20})_s$O— wherein s is an integer having a value of 2 to 4 and both oxygens are attached to the same carbon in $R_4$;— $S(CR_{10}R_{20})_s$S—wherein s is as previously defined and both sulfurs are attached to the same carbon in $R_4$; cycloalkyl, or cycloalkyl alkyl group; a halosubstituted $C_{1-4}$ alkyl, such as $CF_3$; an optionally substituted aryl, such as phenyl, or an optionally substituted arylalkyl, such as benzyl or phenethyl, heteroaryl, or heteroarylalkyl, wherein these aryl or heteoaryl moieties may also be substituted one to two times by halogen; hydroxy; hydroxy substituted alkyl; $C_{1-10}$ alkoxy; S(O)m alkyl; amino, mono & di-$C_{1-4}$ alkyl substituted amino, such as in the $NR_9R_{11}$ group (wherein $R_9$ and $R_{11}$ are as defined below); $C_{1-10}$ alkyl, or $CF_3$.

Preferably, $R_4$ is a $C_{1-4}$ alkyl, such as isobutyl, or an alkenyl, such as isobutenyl.

Suitably, $R_9$ and $R_{11}$ are independently hydrogen, $C_{1-10}$ alkyl, aryl, or arylalkyl.

Suitably, $R_{10}$ and $R_{20}$ are independently hydrogen or $C_{1-4}$ alkyl.

Suitably, $R_5$ is hydrogen, $C_{1-10}$ alkyl, aryl, arylalkyl, heteroaryl, heteroarylalkyl, $C(O)_2R_6$, $C(O)R_6$. Preferably $R_5$ is hydrogen, $C(O)_2R_6$, or a heteroaryl ring, and preferably $R_6$ therein is a $C_{1-4}$ alkyl, such as methyl. If $R_5$ is a heteroaryl ring, it is preferably a 2-, 3,- or 4-pyridyl. The alkyl, aryl, arylalkyl, heteroaryl, and heteroarylalkyl may be optionally substituted as herein defined.

Suitably, $R_6$ is $C_{1-10}$ alkyl, aryl, arylalkyl, heteroaryl, heteroarylalkyl, heterocyclic, or heterocyclicalkyl. The aryl, arylalkyl, heteroaryl, heteroarylalkyl, heterocyclic, and heterocyclicalkyl moieties may be optionally substituted as herein defined.

Suitably, $R_7$ is independently hydrogen, $C_{1-10}$ alkyl, aryl, arylalkyl, heteroaryl, heteroarylalkyl, heterocyclic, or heterocyclicalkyl. The alkyl, aryl, arylalkyl, heteroaryl, heteroarylalkyl, heterocyclic, and heterocyclicalkyl moieties may be optionally substituted as herein defined.

Suitable pharmaceutically acceptable salts are well known to those skilled in the art and include basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, salicylic acid, phenylacetic acid and mandelic acid The following terms, as used herein, refer to:

"halo"—all halogens, that is chloro, fluoro, bromo and iodo;

"$C_{1-10}$ alkyl" or "alkyl"—both straight and branched chain radicals of 1to 10 carbon atoms, unless the chain length is otherwise limited, including, but nor limited to, methyl, ethyl, n-propyl, iso-propyl, n-butyl, sec-butyl, iso-butyl, teri-tbutyl, and the like;

"cycloalkyl" is used herein to mean cyclic radicals, preferably of 3 to 8 carbons, including but not limited to cyclopropyl, cyclopentyl, cyclohexyl, and the like;

"alkenyl" is used herein at all occurrences to mean straight or branched chain radical of 2–10 carbon atoms, unless the chain length is limited thereto, including, but not limited to ethenyl, 1-propenyl, 2-propenyl, 2-methyl-1-propenyl, 1-butenyl, 2-butenyl and the like, "aryl"—phenyl and naphthyl;

"heteroaryl" (on its own or in any combination, such as "heteroaryloxy", or "heteroaryl alkyl")—a 5–10 membered aromatic ring, system in which one or more rings contain one or more heteroatoms selected from the gyrouip consisting of N, O, or S, such as, but not limited, to pyrrole, pyrazole, furan, thiophene, quinoline, isoquinoline, quinazolinyl, pyridine, pyrimidine, oxazole, thiazole, thiadiazole, triazole, imidazole, or benzimidazole;

"heterocyclie" (on its own or in any combination, such as "heterocyclylalkyl")—a saturated or partially unsaturated 4–10 membered ring system in which one or more rings contain one or more heteroatoms selected from the group consisting of N, O, or S; such as, but not limited to, pyrrolidine, piperidine, piperazine, morpholine, tetrahydropyran, or imidazolidine;

The term "aralkyl" or "heteroarylalkyl" or "heterocyclicalkyl" is used herein to mean $C_{1-4}$ alkyl as defined above attached to an aryl, heteroaryl or heterocyclic moiety as also defined herein unless otherwise indicate;

"sulfinyl"—the oxide S(O) of the corresponding sulfide, the term "thio" refers to the sulfide, and the term "sulfonyl" refers to the fully oxidized $S(O)_2$ moiety;

"aroyl"—a C(O)Ar, wherein Ar is as phenyl, naphthyl, or aryl alkyl derivative such as defined above, such group include but are note limited to benzyl and phenethyl;

"alkanoyl"—a C(O)$C_{1-10}$ alkyl wherein the alkyl is asdefined above.

"optionally substituted" unless specifically defined herein, shall mean such groups as halogen, such as fluorine, chlorine, bromine or iodine; hydroxy; hydroxy substituted $C_{1-10}$ alkyl; $C_{1-10}$ alkoxy, such as methoxy or ethoxy; S(O)m alkyl, wherein m is 0, 1 or 2, such as methyl thio, methylsulfinyl or methyl sulfonyl; amino, mono & di-substituted amino, such as in $NR_9R_{11}$ group; $C_{1-10}$ alkyl, cycloalkyl, or cycloalkyl alkyl group, such as methyl, ethyl, propyl, isopropyl, t-butyl, etc. or cyclopropyl methlyl; halosubstituted $C_{1-10}$ alkyl, such as $CF_3$; an optionally substituted aryl, such as phenyl, or an optionally substituted arylalkyl, such as benzyl or phenethyl, wherein these aryl moieties may also be substituted one to two times by halogen; hydroxy; hydroxy substituted alkyl; $C_{1-10}$ alkoxy; S(O)m alkyl; amino, mono & di-$C_{1-4}$ alkyl substituted amino, such as in the $NR_9R_{11}$ group; $C_{1-10}$ alkyl, or $CF_3$.

As used herein, the terms "alkyl lysophospholipid" (ALP), "alkyl lysophospholipid analog," and "ether-linked phospholipid and analogs thereof" are well known terms to those of skill in the art and need no additional definitions. Generally these terms will encompass compounds that are ether linked phospholipids with alkyl chains in the sn-1 position of the glycerol backbone. These compounds may be derivatives of 1-O-alkyl-2-O-methyl-rac-glycero-3-phosphocholine, derivatives of 1-O-hexadecyl-2-acetal-sn-glycero-3-phosphocholine (PAF), derivatives of esterlysophosphiolipid (2-PLC), or derivatives of lysophosphatidylcholine (2-LPC). Etherlysophospholipids are also referred to as alkyllysoPC's, or ALPs; alkylphosphocholines are also referred to as APCs; a hexadecyl phosphocholine is referred to as HPC. Suitable compounds encompassed by this term, include but are not limited to, those described in Schick et al., Lipids, 22 (11) 904–910 (1987); such as those described in Morris-Natschke et al., J. Med. Chem., 29 (10) 2114–2117 (1986); Goto et al., Anti-cancer Research, 14:357362 (1994); Langen et al., Anticancer Research, 12:2109–2112 (1992); Volger et al., Lipids, 28(6) 511–516 (1993); Workman et al., Biochem. Pharm., 41(2) 319–22 (1991); Kohler et al., Inflammation, 17(3), 245–261 (1993); Brachwitz et al., Lipids, 22 (11) 897–903 (1987); Berdel, W., Lipids, 22(11) 970–973 (1987); Danhauser et al., Lipids, 22(11) 911–915 (1987); Danhauser-Riedl et al., J. Lipid Metabolism, 2, 271–280 (1990); Lohmeyer et al., Biochem. Pharm., 45 (1) 77086 (1993); Ries, et al., Chemistry and Physics of Lipids, 61, 225–234 (1992); as well as derivatives having sulfur and nitrogen linkages, such as Guivisdalsky et al., J. Med. Chem., 33 (9), 2614–2621 (1990); and Pignol et al., Anti-Cancer Drugs, 3, 599–608 (1992) whose disclosures are incorporated by reference in their entirety herein.

It is recognized that the compounds of the present invention may exist as stereoisomers, regioisomers, or diastereoisomers. These compounds may contain one or more asymmetric carbon atoms and may exist in racemic and optically active forms. All of these compounds are included within the scope of the present invention.

Specifically exemplified compounds of Formula (I) are:

(3RS,4RS)-4-(Isobutoxy)-3-(triphenylmethylamino) azetidin-2-one (3R,4R)-4-(Isobutoxy)-3-(triphenylmethylamino)azetidin-2-one (3S,4S)-4-(Isobutoxy)-3-(triphenylmethylamino)azetidin-2-one (3R,4R)-4-(Isobutylthio)-3-(triphenylmethylamino) azetidin-2-one (3R,4R)-4-(Isobutylsulfonyl)-3-(triphenylmethylamino) azetidin-2-one (3S,4R)-4-(Isobutoxy)-3-(triphenylmethylamino)azetidin-2-one (3S,4R)-4-(Propoxy)-3-(triphenylmethylamino)azetidin-2-one (3S,4S)-4-(Propoxy)-3-(triphenylmethylamino)azetidin-2-one (3S,4R)-4-(Benzyloxy)-3-(triphenylmethylamino)azetidin-2-one
(3S,4S)-4-(Benzyloxy)-3-(triphenylmethylamino)azctidin-2-one
(3S,4R)-4-Methoxy-3-(triphenylmethylamino)azetidin-2-one
(3S,4R)-4-(Isobutenyloxy)-3-(triphenylmethylamino)azetidin-9-one
(3S,4R)-4-Octyloxy-3-(triphenylmethylamino)azetidin-2-one
(3S,4R)-4-Phenoxy-3-(triphenylmethylamino)azetidin-2-one
(3S,4S)-4-Phenoxy-3-(triphenylmethylamino)azetidin-2-one
(3S,4R)-3-[[(4-Iodophenyl)diphenylmethyl]amino]-4-(isobutoxy)azetidin-2-one
(3S,4S)-4-[3-(Methoxycarbonyl)propoxy]-3-(triphenylmethylamino)azetidin-2-one
(3S,4R)-4-[[2-(3-Pyridylmethyl)-1,3-dithian-2-yl]methoxy]-3-(triphenylmethylamino)-azetidin-2-one
(3S,4S)-4-(Prop-2-ynyloxy)-3-(triphenylmethylamino)azetidin-2-one
Methyl 4-[(3S,4S)-2-oxo-3-(triphenylmethylamino)azetidin-4-yloxy]but-2-ynoate
Methyl 4-[(3S,4R)-2-oxo-3-(triphenylmethylamino)azetidin-4-yloxy]but-2-ynoate
(3S,4R)-4-[(2(5H)Furanon-4-yl)methoxy]-3-(triphenylmethylamino)azetidin-2-one
(S)-3-(Triphenylmethylamino)azetidin-2-one
(RS)-3-(Triphenylmethylamino)azetidin-2-one
(3R,4R)-4-(Methylsulfonyl)-3-(triphenylmethylamino)azetidin-2-one Compounds of formula (I) where 4-(X—R⁴) is 4-(O—R⁴) or 4-(S—R⁴) can be prepared according to Scheme I from 1, where R³ is defined as in formula (I) and Y is a suitable leaving group such as methylsulfonyl, acyloxy, or chloro. Compounds 1, where Y is methylsulfonyl, are obtained as described in J. Chem. Soc. Perkin I, 447, 1976 whose disclosure is incorporated herein by reference. The displacement of group Y in 1 with HO—R⁴ or HS—R⁴ may be carried out with a suitable catalyst such as zinc acetate in a suitable solvent such as toluene at a suitable temperature such at 90° C. Alternatively, with phenols, the displacement may be carried out in the presence of a suitable base, such as aqueous sodium hydroxide, in a suitable solvent such as acetone.

Compound 3 where 4-(X—R⁴) is 4-(SO—R⁴) and 4-(SO₂—R⁴) and R³, R⁴ are defined as in formula (I), can be obtained by further oxidation of 2 where 4-(X—R⁴) is 4-(S—R⁴) with a suitable organic oxidizing agent such as m-chloroperbenzoic, peracetic acid, etc. in a suitable solvent such as dichloromethanc. or by further oxidation with a suitable inorganic oxidizing agent such as sodium periodate or potassium permangante in a solvent such as water, acetone or acetic acid.

Scheme I

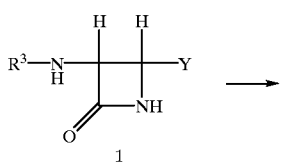

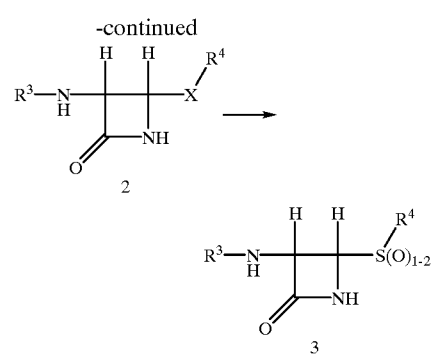

Alternatively, compounds of formula (I) may be prepared according to Scheme II from 4. Compound 4, wherein X is O—R⁴ or S—R⁴ and R⁴ is as defined in formula (I) and R¹ is hydrogen, can be prepared from 4-acetoxy or 4-benzoyloxy-azetidin-2-one as described in Synthetic Communications, 24, 131–135 (1994) whose disclosure is incorporated herein by reference. Treatment of 4, where R¹ is hydrogen, with a suitable silylating group such as tert-butyldimethylsilyl chloride and a suitable base such as triethylamine in a suitable solvent such as tetrahydrofuran gives 4 where R¹ is tert-ibutyldimethylsilyl. Treatment of 4, where R¹ is tert-butyldimethylsilyl, with a suitable base such as lithium diisopropylamide in a suitable solvent such as tetrahydrofuran at a suitable temperature such as −50° C., followed by addition to a solution of a suitable azidating reagent such as tosyl azide in a suitable solvent such as tetrahydrofuran, followed by treatment with trimethylsilyl chloride gives 5 where R¹ is tert-butyldimethylsilyl. Reduction of the azido group in 5, where R¹ is tert-butyldimethylsilyl, with a suitable reducing agent such as hydrogen sulfide in a suitable solvent such as dichloromethane containing a suitable base such as triethylamine gives 6 where R¹ is tert-butyldimethylsilyl. Treatment of 6, where R¹ is tert-butyldimethylsilyl, with a suitable alkylating agent R³Z, where R³ is as defined in formula (I) and Z is a suitable leaving group such as chloro, in a suitable solvent such as dimethylformamide containing a suitable base such as dilsopropylethylamine, gives 2 where R¹ is tert-butyldimethylsilyl. Treatment of 2, where R¹ is tert-butyldilmethylsilyl, with a suitable inorganic fluoride, such as tetrabutylammonium flruroride, in a suitable solvent such as tetrahydrofuran and acetic acid gives 2 where R¹ is hydrogen.

Scheme II

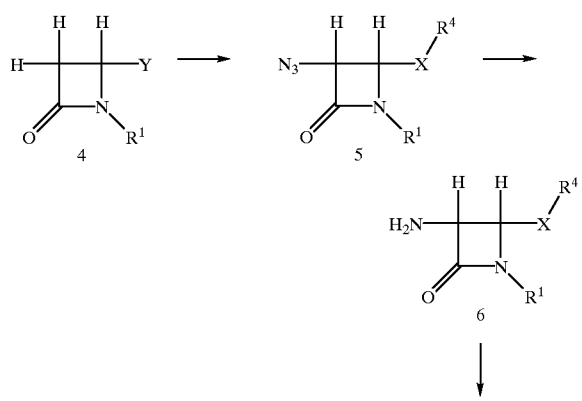

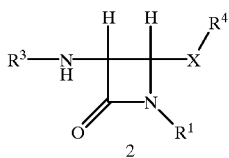

Alternatively, compounds II-5 may be prepared using [2+2] cycloaddition reactions, for example, by following the general procedures described in Cama et. al., Tetrahedron Letters, 4233, 1978, whose disclosure is incorporated herein by reference.

SYNTHETIC CHEMISTRY

The invention will now be described by reference to the following examples which are merely illustrative and are not to be construed as a limitation of the scope of the present invention. All temperatures are given in degrees centigrade, all solvents are highest available purity and all reactions run under anhydrous conditions in an argon atmosphere unless otherwise indicated.

In the Examples, all temperatures are in degrees Centigrade (° C.). Mass spectra were performed upon a VG Zab mass spectrometer using fast atom bombardment, unless otherwise indicated. $^1$H-NMR (hereinafter "NMR") spectra were recorded at 250 MHz using a Bruker AM 250 or Am 400 spectrometer. Multiplicities indicated are: s=singlet, d=doublet, t=triplet, q=quartet, m=multiplet and br indicates a broad signal. Sat. indicates a saturated solution, eq indicates the proportion of a molar equivalent of reagent relative to the principal reactant.

Flash chromatography is run over Merck Silica gel 60 (230–400 mesh).

Example 1

Preparation of (3RS,4RS)-4-(Isobutoxy)-3-(triphenylmethylamino)azetidin-2-one a). 4-(Isobutoxy)azetidin-2-one A mixture of 4-(benzoyloxy)azetidin-2-one (15.2 g, 80 mmol) in toluene (150 mL) was treated with isobutanol (12 g, 0.16 mol), triethylamine (16 g, 0.16 mol) and palladium acetate (3.6 g, 16 mmol), stirred in an ice bath for several hours, allowed to warm to RT and stirred for 16 h. The mixture was filtered through Supercel, concentrated and the residue was chromatographed on silica gel eluted with 10–35% ethyl acetate:hexane. Fractions containing the product were combined, concentrated and rechromatographed on silica gel eluted with 10–25% ethyl acetate:hexane to give the title compound (4.9 g).

b). 1-tert-Butyldimethylsilyl-4-(isobutoxy)azetidin-2-one

A solution of 4-(isobutoxy)azetidin-2-one (4.8 g, 33 mmol) in tetrahydrofuran (50 mL) was stirred in an ice bath and treated with triethylamine (6.6 mL, 66 mmol) followed by dropwise addition of a solution of tert-butyldimethylsilyl chloride (6.5 g, 43 mmol) in tetrahydrofuran (15 mL). The mixture was stirred for 5 h in the cold and stored in the refrigerator for 64 h. The mixture was poured into cold water, extracted with ethyl acetate, and the combined organic phase was washed with brine, dried (magnesium sulfate), and concentrated. The residue was chromatographed on silica gel eluted with 10% ethyl acetate:hexane. Fractions containing the product were pooled and concentrated to give the title compound (6.6 g, 79%).

c). (3RS,4RS)-3-Azido-1-(tert-butyldimethylsilyl)-4-(isobutoxy)azetidin-2-one

A solution of N-(isopropyl)cyclohexylamine (1.5 g, 10 mmol) in tetrahydrofuran (18 mL) was cooled to −15° C. and 2M butyllithium (48 mL, 10 mmol) was added dropwise. The reaction mixture was stirred for 40 min, the temperature was lowered to −70° C., and the mixture was treated dropwise over 10 min with a solution of 1-(tert-butyldimethylsilyl)-4-(isobutoxy)-azetidin-2-one (1.8 g, 7 mmol) in tetrahydrofuran (7 mL). The mixture was stirred for 1 h, transferred to a jacketed addition funnel maintained at −70° C., and added over 40 min to a solution of p-toluenesulfonyl azide (1.8 g, 9 mmol) in tetrahydrofuran (8 mL) containing hexamethylphosphoramide (2 mL) maintained at −70° C. The reaction was stirred for 1 h and at −50° C. for 4.5 h. The mixture was stirred at −28° C. for 16 h, and trimethylsilyl chloride (5 mL) was added and the mixture was stirred at RT for 45 min. The mixture was diluted with water and extracted with ethyl acetate. The combined organic phases were washed with brine, dried (magnesium sulfate) and concentrated. The residue was chromatographed on silica gel eluted with 10% ethyl acetate:hexane to give the title compound (0.6 g, 30%). MS(ES) m/e 299 [M+H]$^+$.

d). (3RS,4RS)-3-Amino-1-(tert-butyldimethylsilyl)-4-(isobutoxy)azetidin-2-one

A solution of (3RS,4RS)-3-azido-1-(tert-butyldimethylsilyl)-4-(isobutoxy)azetidin-2-one (0.2 g, 0.67 mmol) in dichloromethane (15 mL) containing triethylamine (0.07 g, 0.7 mmol) was cooled in an ice bath and hydrogen sulfide was bubbled through the solution gently for 10 min. The mixture was stirred in the cold for 4 h, concentrated, and then treated with dichloromethane and concentrated four times to give the title compound.

e). (3RS,4RS)-1-(tert-Butyldimethylsilyl)-4-(isobutoxy)-3-(triphenylmethylamino)azetidin-2-one A solution of (3RS,4RS)-3-amino-1-(tert-butyldimethylsilyl)-4-(isobutoxy)azetidin-2-one (0.2 g) was dissolved in dimethylformamide (8 mL), cooled in an ice bath, and treated with diisopropylethylamine (0.1 mL) followed by trityl chloride (167 mg, 0.6 mmol). The mixture was stirred for 18 h, diluted with water (40 mL) and extracted with ethyl acetate. The combined organic phase was dried (magnesium sulfate), concentrated, and the residue was chromatographed on silica gel eluted with 20% ethyl acetate:hexane to give the title compound. MS(ES) m/e 515 [M+H]$^+$.

f). (3RS,4RS)-4-(Isobutoxy)-3-(triphenylmethylamino)azetidin-2-one

A solution of (3RS,4RS)-1-(tert-butyldimethylsilyl)-4-(isobutoxy)-3-(triphenylmethylamino)azetidin-2-one (160 mg, 0.3 mmol) in tetrahydrofuran (4 mL) was cooled in an ice bath and treated with acetic acid (25 mg, 0.4 mmol) followed by dropwise addition of 1M tetrabutylammonium fluoride (0.6 mL, 0.6 mmol). The mixture was stirred for 20 min and passed through silica gel (10 g) eluted with ethyl acetate. The eluate was concentrated and the residue was chromatographed on silica gel eluted with 20% ethyl acetate:hexane to give the title compound. MS(ES) m/e 423 [M+Na]$^+$.

Example 2

Preparation of (3R,4R)- and (3S,4S)-4-(Isobutoxy)-3-(triphenylmethylamino)azetidin-2-one (3RS,4RS)-4-(Isobutoxy)-3-(triphenylmethylamino)azetidin-2-one was resolved by HPLC (Chiralcel OD, 21×250 mm, 10 mL/min, gradient, A:ethanol B:hexane, 0.5–2.5% A during 20 min, UV detection at 254 nm) to afford the title compounds:

(3R,4R)-4-(isobutoxy)-3-(triphenylmethylaiino)azetidin-2-one, $t_R$ 35 min. MS(ES) m/e 801 [2M+H]$^+$, and (3S,4S)-4-(isobutoxy)-3-(triphenylmethylamino) azetidin-2-one, $t_R$ 39.9 min. MS(ES) m/e 801 [2M+H]$^+$.

Example 3

Preparation of (3R4R)-4-(Isobutylthio)-3-(triphenylmethylamino)azetidin-2-one

A solution of zinc acetate (0.7 g, 3 mmol) in toluene (15 mL) and 2-methyl-propanethiol (0.72 g, 8 mmol) was refluxed for 45 min in an apparatus equipped with a Dean-Stark trap to azeotrope water. (3R,4R)-4-(Methylsulfonyl)-3-(triphenylmethylamino)azetidin-2-one (1.5 g, 36 mmol) was added and the mixture was heated to 90° C. for 2 h. The mixture was concentrated and the residue was triturated with ethyl acetate and the insoluble material was removed by filtration. The filtrate was concentrated and the residue was chromatographed on silica gel eluted with 20% ethyl acetate:hexane. The fractions containing the product were combined, concentrated to give the title compound. MS(ES) m/e 417 [M+H]$^+$.

Example 4

Preparation of (3R4R)-4-(Isobutylsulfonyl)-3-(triphenylmethylamino)azetidin-2-one A solution of (3R,4R)-4-(isobutylthio)-3-(triphenylmethylamino)azetidin-2-one (50 mg, 0.12 mmol) in dichloromethane (2 mL) was cooled in an ice bath and treated with m-chloroperbenzoic acid (44 mg, 0.25 mmol). The mixture was stired for 2.5 h in the cold and partitioned between 5% sodium carbonate (5 mL) and dichloromethane. The organic phase was washed with 5% sodium carbonate and with brine, dried (magnesium sulfate), filtered and concentrated. The residue was chromatographed on silica gel eluted with 20% ethyl acetatc:hexane and fractions containing the product were pooled and concentrated to give the title compound (25 mg, 47%). MS(ES) m/e 447 [M–H]$^+$.

Examples 5–13

The following compound have been prepared using the procedure of Example 3, except substituting isobutanol, propanol, benzyl alcohol, methanol, isobutenol, or octanol for 2-methyl-propanethiol gave:

Example 5

(3S,4S)-4-(Isobutoxy)-3-(triphenylmethylamino)azetidin-2-one: MS(ES) m/e 801 [2M+H]$^+$;

Example 6

(3S,4R)-4-(Isobutoxy)-3-(triphenylmethylamino)azetidin-2-one: MS(ES) m/e 401 [M+H]$^+$;

Example 7

(3S,4R)-4-(Propoxy)-3-(triphenylmethylamino)azetidin-2-one: MS(ES) m/e 387 [M+H]$^+$;

Example 8

(3S,4S)-4-(Propoxy)-3-(triphenylmethylamino)azetidin-2-one: MS(ES) m/e 773 [2M+H]$^+$;

Example 9

(3S,4R)-4-(Benzyloxy)-3-(triphenylmethylamino)azetidin-2-one: MS(ES) m/e 435 [M+H]$^+$;

Example 10

(3S,4S)-4-(Benzyloxy)-3-(triphenylmethylamino)azetidin-2-one: MS(ES) m/e 435 [M+H]$^+$;

Example 11

(3S,4R)-4-Methoxy-3-(triphenylmethylamino)azetidin-2-one: MS(ES) m/e 359 [M+H]$^+$;

Example 12

(3S,4R)-4-(Isobutenyloxy)-3-(triphenylmethylamino) azetidin-2-one: MS(ES) m/e 399 [M+H]$^+$;

Example 13

(3S,4R)-4-Octyloxy-3-(triphenylmethylamino)azetidin-2-one: MS(ES) m/e 457 [M+H]$^+$;

Examples 14–15

Preparation of (3S,4R)-4-Phenoxy-3-(triphenylmethylamino)azetidin-2-and (3S,4S)-4-Phenoxy-3-(triphenylmethylamino)azetidin-2-one A solution of phenol (0.3 g, 3.2 mmol) in acetone (3 mL) was treated with 1N sodium hydroxide (3.2 mL, 3.2 mmol), stirred 10 min and treated dropwise with a solution of (3R,4R)-4-methylsulfonyl-3-(triphenylmethylamino) azetidin-2-one (1.2 g, 3 mmol) in acetone (2 mL). The mixture was stirred for 1.5 h, partitioned between water and diethyl ether, and the combined organic phase was washed with brine, dried (magnesium sulfate), and concentrated. The residue was chromatographed on silica gel eluted with 20% ethyl acetate:hexane to give the title compounds:

(3S,4R)-4-phenoxy-3-(triphenylmethylamino)azetidin-2-one: MS(ES) m/e 443 [M+Na]$^+$; 421 [M+H]$^+$;

(3S,4S)-4-phenoxy-3-(triphenylmethylamino)azetidin-2-one: MS(ES) m/e 841 [2M+H]$^+$; 419 [M–H]$^-$.

Example 16

Preparation of (3S,4R)-3-[[(4-Iodophenyl) diphenylmethyl]aminol]-4-(isobutoxy)azetidin-2-one a). (3S,4R)-3-Amino-4-(isobutoxy)azetidin-2-one para-toluenesulfonate A solution of para-toluenesulfonic acid hydrate (190 mg) in acetone (20 mL) was added to a solution of (3S,4R)-4-isobutoxy-3-(triphenylmethylamino)azetidin-2-one (400 mg, 1 mmol) in acetone (20 mL), stirred for 1 h, and concentrated. The residue was triturated with diethyl ether and the resulting solid isolated by filtration to give the title compound (180 mg, 55%).

b). (3S,4R)-3-[[(4-Iodophenyl)diphenylmethyl]amino]-4-(isobutoxy)azetidin-2-one

A solution of (3S,4R)-3-amino-4-(isobutoxy)azetidin-2-one para-toluenesulfonate (180 mg, 0.54 mmol) in acetone (8 mL) containing diisopropylethylamine (1.1 mmol) was treated with a solution of (4-iodophenyl)diphenylmethyl chloride (218 mg, 0.54 mmol), prepared as described by Tschitschibabin, Chem. Ber. 44, 450 (1911), in acetone (98 mL). The solution was stirred for 6 h and partitioned between water and dichloromethane. The combined organic phases were dried (magnesium sulfate), concentrated, and the residue was chromatographed on silica gel eluted with 15% ethyl acetate:hexane to give the title compound (190 mg, 67%). MS(ES) m/e 527 [M+H]$^+$.

Example 17

Preparation of (3S,4S)-4-[3-(Methoxycarbonyl) propoxy]-3-(triphenylmethylamino)azetidin-2-one a). (3S,4S)-3-Amino-4-[3-(methoxycarbonyl)propoxy] azetidin-2-one A solution of methyl 4-[(3S,4S)-2-oxo-3-(triphenylmethylamino)azetidin-4-yloxy]but-2-ynoate (75 mg, 0.17 mmol) in absolute ethanol (6 mL) was treated with 10% palladium-on-carbon (35 mg) and stirred under hydrogen overnight. The catalyst was removed by filtration and the filtrate concentrated. The residual oil was purified on by preparative thin layer chromatography (Whatman, silica gel 60A, 20 ×20 cm, 1000 um, 20% ethyl acetate:hexane). The origin band contained the title compound (30mg). MS(ES) m/e 203.0 [M+H]+.

b). (3S,4S)-4-[3-(Methoxycarbonyl)propoxy]-3-(triphenylmethylamino)azetidin-2-one (3S,4S)-3-Amino-4-[3-(methoxycarbonyl)propoxy]azetidin-2-one (30 mg, 0.148 mmol) was dissolved in dry dichloromethane (2 mL) and treated with triphenylmethyl chloride (41 mg, 0.148 mmol) followed by diisopropylethylamine (19 mg, 0.148 mmol). The solution was stirred at RT under argon for 5 h, diluted with water and extracted with dichloromethane. The organic phases were combined, washed with water and brine, dried (magnesium sulfate), filtered, and concentrated. The residue was purified by preparative thin layer chromatography (Whatman, silica gel 60A, 20 ×20 cm, 1000 um, 40% ethyl acetate:hexane) to give the title compound (7 mg). MS(ES) m/e 445.2 [M+H].

Examples 18–21

The following compounds were prepared using the general procedure of Example 3, except substituting:

Examples 18 and 19 methyl 4-hydroxy-2-butynoate (Zh. Obshch. Khim. 66, 106, 1996),

Example 20

4-hydroxymethyl-2(5H)-furanone, (J. Chem. Res., Synop. 222, 1986), or

Example 21

2-(3-pyridylmethyl)-1,3-dithianyl-2-methanol for 2-methyl-propanethiol used therein.

Preparation of Example 18

Methyl 4-[(3S,4S)-2-oxo-3-(triphenylmethylamino) azetidin-4-yloxy]but-2-ynoate

Methyl 4-[(3S,4S)-2-oxo-3-(triphenylmethylamino) azetidin-4-yloxy]but-2-ynoate: $^1$H NMR(270 MHz, CDCl$_3$) δ 3.54 (d, J=17 Hz, 1H), 3.77 (s, 3H), 3.83 (d, J=17 Hz, 1H, 4.08 (s, 1H), 4.11 (d, J=1.1 Hz, 1H), 6.39 (s, 1H), 7.19–7.53 (m, 15H); IR(CHCl$_3$) 3330, 2240, 1770, 1718, 1477, 1445, 1434, 1260, 1194, 1166, 940, 759, 706 cm$^{-1}$.

Example 19

Methyl 4-[(3S,4R)-2-oxo-3-(triphenylmethylamino) azetidin-4-yloxy]but-2-ynoate

Methyl 4-[(3S,4R)-2-oxo-3-(triphenylmethylamino) azetidin-4-yloxy]but-2-ynoate: $^1$H NMR(60 MHz, CDCl$_3$) δ 2.9 (d, J=9 Hz, 1H), 3.70 (s, 3H), 3.60 (d, J=17 Hz, 1H), 3.93 (d, J=17 Hz, 1H), 4.0–4.3 (m, 2H), 6.8 (s, 1H), 7.2–7.8 (m, 15H); IR(CHCl$_3$) 3350, 1775, 1715 cm$^{-1}$.

Example 20

(3S,4R)-4-[(2(5H)Furanon-4-yl)methoxy]-3-(triphenylmethylamino)azetidin-2-one
(3S,4R)-[(2(5H)furanon-4-yl)methoxy]-3-(triphenylmethylamino)azetidin-2-one: $^1$H NMR(60 MHz, CDCl$_3$) δ 2.8 (d, J=9 Hz, 1H), 3.9 (m, 2H), 4.2 (m, 2H), 4.53 (m, 2H), 5.87 (m, 1H), 7.0–8.7 (m, 17H); IR(CHCl$_3$) 1785, 1755, 1650 cm$^{-1}$.

Example 21

(3S,4R)-4-[[2-(3-Pyridylmethyl)-1,3-dithian-2-yl]methoxy]-3-(triphenylmethylamino)azetidin-2-one
(3S,4R)-4-[[2-(3-pyridylmethyl)-1,3-dithian-2-yl]methoxy]-3-(triphenylmethylamino)azetidin-2-one: IR(CHCl$_3$) 3370, 1775 cm$^{-1}$.

Using analagous procedures to those indicated above, or as indicated, the following compounds have been syntheized:

Example 22

(3S,4S)-4-(Prop-2-ynyloxy)-3-(triphenylmethylamio) azetidin-2-one
J. Chem. Soc. Perkin Trans. I 2268, 1979;

Example 23

(3R,4R)-4-(Methylsulfonyl)-3-(triphenylmethylamino) azetidin-2-one
J. Chem. Soc. Perkin Trans. I 2268, 1979;

Example 24

(3S,4R)-4-(Isobutenyloxy)-3-(triphenylmethylamino) azetidin-2-one
J. Chem. Soc. Perkin Trans. I 2268, 1979;

Example 25

(S)-3-(Triphenylmethylamino)azetidin-2-one
Tetr. Letters 30, 3219, 1989.

Example 26

Using analagous procedures to those noted therein, the racemic mixture of (RS)-3-(Triphenylmethylamino) azetidin-2-one may be produced.

METHODS OF TREATMENT

The compounds of Formula (I) or pharmaceutically acceptable salts thereof can be used in the manufacture of a medicament for the prophylactic or therapeutic treatment of an proliferative disease state in a manrmal, preferably a human. Disease states which could benefit from the inhibition of cell proliferation include, but are not limited to, rheumatoid arthritis, psoriasis, atherosclerosis, and cancers such as leukemia or solid tumors.

Inhibition of CoA-IT and the blockade of proliferation in diseased cells according to this invention is of therapeutic benefit in a broad range of diseases or disorders. The invention herein is therefore useful to treat such disease states both in humans and in other mammals.

The compounds of Formula (I) or pharmaceutically acceptable salts thereof can be used in the treatment of proliferative diseases either as sole treatment or in combination with other treatments that also inhibit proliferation. Examples of such treatments include, but are not limited to, cancer chemotherapeutic drugs and radiation therapy. Many antiproliferative drugs show additive or potentiating effectiveness when used in combination with other antiproliferative drugs, as in the standard therapies of numerous cancers.

In order to use a compound of formula (I) or a pharmaceutically acceptable salt thereof in therapy, it will normally be formulated into a pharmaceutical composition in accordance with standard pharmaceutical practice. This invention, therefore, also relates to a pharmaceutical composition comprising an effective, non-toxic amount of a compound of formula (I) and a pharmaceutically acceptable carrier or diluent.

Compounds of formula (I), pharmaceutically acceptable salts thereof and pharmaceutical compositions incorporating such may conveniently be administered by any of the routes conventionally used for drug administration, for instance, orally, topically, parenterally or by inhalation. The compounds of formula (I) may be administered in conventional dosage forms prepared by combining a compound of formula (I) with standard pharmaceutical carriers according to conventional procedures. Such pharmaceutically acceptable carriers or diluents and methods of making are well known to those of skill in the art, and reference can be found in such texts as Remington's Pharmaceutical Sciences, 18th Ed., Alfonso R. Genarao, Ed., 1990, Mack Publishing Co. and the Handbook of Pharmaceutical Excipents, APhA Publications, 1986.

The compounds of formula (I) may also be administered in conventional dosages in combination with known second therapeutically active compounds, such as anticancer, or antiproliferative drugs for instance. These procedures may involve mixing, granulating and compressing or dissolving the ingredients as appropriate to the desired preparation. It will be appreciated that the form and character of the pharmaceutically acceptable carrier or diluent is dictated by the amount of active ingredient with which it is to be combined, the route of administration and other well-known variables. The carrier(s) must be "acceptable" in the sense of being compatible with the other ingredients of the formulation and not deleterious to the recipient thereof.

The pharmaceutical carrier employed may be, for example, either a solid or liquid. Exemplary of solid carriers are lactose, terra alba, sucrose, talc, gelatin, agar, pectin, acacia, magnesium stearate, stearic acid and the like. Exemplary of liquid carriers are syrup, peanut oil, olive oil, water and the like. Similarly, the carrier or diluent may include time delay material well known to the art, such as glyceryl mono-stearate or glyceryl distearate alone or with a wax.

A wide variety of pharmaceutical forms can be employed. Thus, if a solid carrier is used, the preparation can be tableted, placed in a hard gelatin capsule in powder or pellet form or in the form of a troche or lozenge. The amount of solid carrier will vary widely but preferably will be from about 25 mg. to about 1 g. When a liquid carrier is used, the preparation will be in the form of a syrup, emulsion, soft gelatin capsule, sterile injectable liquid such as an ampule or nonaqueous liquid suspension.

Compounds of formula (I) may be administered topically, that is by non-systemic adrninistration. This includes the application of a compound of formula (I) externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Formulations suitable for topical administration include liquid or semi-liquid preparations suitable for penetration through the skin to the site of inflammation such as liniments, lotions, creams, ointments or pastes, and drops suitable for admninistration to the eye, ear or nose. The active ingredient may comprise, for topical administration, from 0.001% to 10% w/w, for instance from 1% to 2% by weight of the formulation. It may however comprise as much as 10% w/w but preferably will comprise less than 5% w/w, more preferably from 0.1% to 1% w/w of the formulation.

Lotions according to the present invention include those suitable for application to the skin or eye. An eye lotion may comprise a sterile aqueous solution optionally containing a bactericide and may be prepared by methods similar to those for the preparation of drops. Lotions or liniments for application to the skin may also include an agent to hasten drying and to cool the skin, such as an alcohol or acetone, and/or a moisturizer such as glycerol or an oil such as castor oil or arachis oil.

Creams, ointments or pastes according to the present invention are semi-solid formulations of the active ingredient for external application. They may be made by mixing the active ingredient in finely-divided or powdered form, alone or in solution or suspension in an aqueous or non-aqueous fluid, with the aid of suitable machinery, with a greasy or non-greasy base. The base may comprise hydrocarbons such as hard, soft or liquid paraffin, glycerol, beeswax, a metallic soap; a mucilage; an oil of natural origin such as almond, corn, arachis, castor or olive oil; wool fat or its derivatives or a fatty acid such as steric or oleic acid together with an alcohol such as propylene glycol or a macrogel. The formulation may incorporate any suitable surface active agent such as an anionic, cationic or non-ionic surfactant such as a sorbitan esteror a polyoxyethylene derivative thereof. Suspending agents such as natural gums, cellulose derivatives or inorganic materials such as silica-ceous silicas, and other ingredients such as lanolin, may also be included.

Drops according to the present invention may comprise sterile aqueous or oily solutions or suspensions and may be prepared by dissolving the active ingredient in a suitable aqueous solution of a bactericidal and/or fungicidal agent and/or any other suitable preservative, and preferably including a surface active agent. The resulting solution may then be clarified by filtration, transferred to a suitable container which is then sealed and sterilized by autoclaving or maintaining at 98–100° C. for half an hour. Alternatively, the solution may be sterilized by filtration and transferred to the container by an aseptic technique. Examples of bactericidal and fungicidal agents suitable for inclusion in the drops are phenylmercuric nitrate or acetate (0.002%), benzalkonium chloride (0.01%) and chlorhexidine acetate (0.01%). Suitable solvents for the preparation of an oily solution include glycerol, diluted alcohol and propylene glycol.

Each dosage unit for oral administration contains preferably from 1 to 250 mg (and for parenteral administration contains preferably from 0.1 to 25 mg) of a compound of formula (I) or a pharmaceutically acceptable salt thereof calculated as the free base.

The pharmaceutically acceptable compounds of the invention will normally be administered to a subject in a daily dosage regimen. For an adult patient this may be, for example, an oral dose of between 1 mg and 500 mg, preferably between 1 mg and 250 mg, or an intravenous, subcutaneous, or intramuscular dose of between 0.1 mg and 100 mg, preferably between 0.1 mg and 25 mg, of the compound of the Formula (I) or a pharmaceutically acceptable salt thereof calculated as the free base, the compound being administered from 1 to 4 times per day.

The choice of form for administration, as well as effective dosages, will vary depending, inter alia, on the condition being treated. The choice of mode of administration and dosage is within the skill of the art.

BIOLOGICAL METHODS

To determine activity of the compounds of Formula (I) various cellular assays can be used to determine in vitro activity. Described herein is an in vitro assay for CoA-IT enzyme activity. Several assays for measuring cell proliferation and/or apoptosis are also described, both for in vitro and ex vivo.

In Vitro Assays

Assay: CoA-IT Activity

The following is a method to measure CoA-IT activity and the effects of compounds on CoA-IT activity. The assay is based upon mixing cellular material containing CoA-IT activity with a stable lyso phospholipid such as 1-alkyl-2-acyl-GPC and measuring the production of phospholipid product such as 1-alkyl-2-acyl-GPC occurring in the absence of added CoA or CoA-fatty acids.

Cell Preparation

Any inflammatory cell that contains high levels of CoA-IT activity can be used, such as neutrophils, macrophages or cell lines such as U937 cells. U937 cells were obtained from American Type Culture Collection and grown in RPMI-1640 media (Gibco, Grand Island, N.Y.) supplemented with 10% fetal bovine serum (Hyclone, Logan, UT) at 37° C., 5% $CO_2$. Cells were grown without differentiation (basal state) by any agent, such as dimethyl sulfoxide. As used herein, "inflammatory cells" include, but are not limited to neutrophils, macrophages, monocytes, lymphocytes, eosinophils, basophils, and mast cells.

Microsomal preparation

Microsomes were prepared using standard techniques. In this case, cells were washed with a buffer of 250 mM sucrose, 10 mM Tris, 1 mM EGTA, 1 mM $MgCl_2$, pH 7.4 and ruptured by $N_2$ cavitation (750 psi, 10 minutes). The ruptured cells were centrifuged 1000×g, 5 minutes. The resulting supernatant was centrifuged at 20,000×g,~20 minutes. Microsomes were prepared from this supernatant by centrifugation at 100,000×g, 60 minutes. The resulting pellet was washed once with assay buffer (150 mM NaCl, 10 mM $Na_2KPO_4$, 1 mM EGTA, pH 7.4), recentrifuged and the pellet resuspended in assay buffer (4–20 mg protein/ml) and was stored at −80° C. until assayed.

CoA-IT activity

CoA-II activity was measured in 1.5 ml centrifuge tubes in a total volume of 100 ul. Microsomes were diluted in assay buffer to the desired protein concentration (6–20 ug/tube). The reaction was initiated by addition of [3H]1-alkyl-2-lyso-sn-glycero-3-phosphocholine (GPC) (~0.1 uCi/tube) and 1 $\mu$M final cold 1-alkyl-2-lyso-GPC in assay buffer with 0.25 mg/ml fatty acid-poor bovine serum albumin (BSA) (Calbiochem, La Jolla, Calif.). [3H]1-alkyl-2-lyso-GPC, approximately 50 Ci/mmol, was from NEN-Dupont (Boston, Mass.) and cold 1-alkyl-2-lyso-GPC was from Biomol (Plymouth Meeting, Pa.). Microsomes were pretreated with desired agents for the desired time (10 minutes) before the addition of [3H]1-alkyl-2-lyso-GPC. The reaction was run for the desired tlime (10 minutes) at 37° C. The reaction was stopped and the lipids extracted by addition of 100 ul of chloroform:methanol (1:2, v/v) followed by 100 ul of chloroform and 100 ul of 1 M KCl. The samples were vortexed and centrifuged at high speed in a microfuge for 2–3 minutes. An aliquot of the chloroform-extracted materials were separated, usually by TLC in chloroform/methanol/acetic acid/water (50:25:8:4, v/v), visualized by radioscanning (Bioscan) and the product, [3H]1-alkyl-2-acyl-GPC, was scraped and quantified by liquid scintillation spectroscopy. With this TLC system, the synthetic standards of 1-alkyl-2-lyso-GPC and 1-alkyl-2-acyl-GPC were well separated, with Rf values of approximately 0.25 and 0.65, respectively. Other methods can be used to separate substrate from product, including but not limited to column chromatography, affinity chromatography and post reaction derivitization.

Protein concentration were assessed using the protein assay reagents from Bio Rad (Richmond, Calif.).

Results

A variety of compounds have been tested in this assay to determine its selectivity and inability to detect trivial, non-selective inhibitors. Inhibitors of 5-lipoxygenase (5-LO) and cyclooxygenase (CO), such as indomethicin, naproxen, 6-(4'-Fluorophenyl)-5-(4-pyridyl)-2,3-dihydroimidzo-[2,1-b]thiazole and 6-(4'-Fluorophenyl)-5-(4-pyridyl)2,3-dihydroimidzo-[2,1-b]thiazole-dioxide had no effect on CoA-IT activity at concentrations up to 100 $\mu$M. The antioxidant BHT also has no effect at concentrations up to 100 $\mu$M. Compounds which complex with phospholipids and inhibit $PLA_2$ activity, such as quinacrine and aristolochic acid have no effect on CoA-IT activity at concentrations up to 500 $\mu$M. Doxepine, a compound reported to inhibit PAF release did not inhibit CoA-IT at concentrations up to 100 $\mu$M. Sodium diclofenac, reported to decrease leukotriene production by altering arachidonic acid metabolism, had no effect on CoA-IT activity at concentrations up to 500 $\mu$M. These results show that the assay for CoA-IT activity is sensitive and selective.

Figure 2:
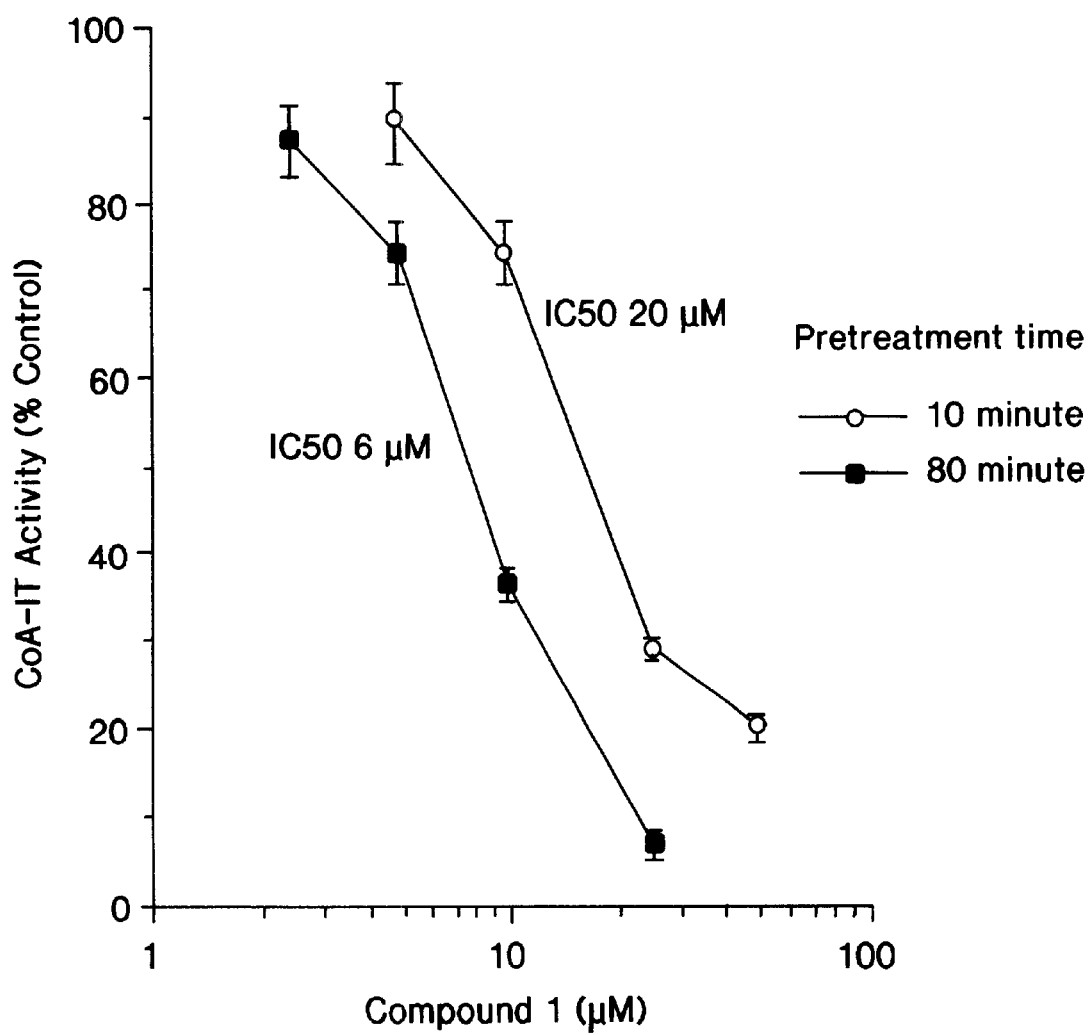
FIG. 2 demonstrates the time dependent inhibition of CoA-IT by (3S,4R)-4-(isobutenyloxy)-3-triphenylmethylamino)azetidin-2-one.

FIG. 2 demonstrates the inhibition of CoA-IT activity in a time dependent manner using a representative compound of Formula (I), Example 24, (3S,4R)-4-(isobutenyloxy)-3-(triphenylmethylamino)azetidin-2-one.

Other representative compounds of Formula (I) which inhibited CoA-IT activity, as a time-dependent inhibitor, in the microsomal CoA-IT assay described above [generally at an $IC_{50}$ of <50 $\mu$M or less, at a 10 min preincubation time] are:

(3RS,4RS)-4-(Isobutoxy)-3-(triphenylmethylamino)azetidin-2-one (3R,4R)-4-(Isobutoxy)-3-(triphenylmethylamino)azetidin-2-one (3S,4S)-4-(Isobutoxy)-3-(triphenylmethylamino)azetidin-2-one (3R,4R)-4-(Isobutylthio)-3-(triphenylmethylamino)azetidin-2-one (3R,4R)-4-(Isobutylsulfony)-3-(triphenylmethylamino)azetidin-2-one (3S,4R)-4-(Isobutoxy)-3-(triphenylmethylamino)azetidin-2-one (3S,4R)-4-(Propoxy)-3-(triphenylmethylamino)azetidin-2-one (3S,4S)-4-(Propoxy)-3-(triphenylmethylamino)azetidin-2-one (3S,4R)-4-(Benzyloxy)-3-(triphenylmethylamino)azetidin-2-one (3S,4S)-4-(Benzyloxy)-3-(triphenylmethylamino)azetidin-2-one (3S,4R)-4-Methoxy-3-(triphenylmethylamino)azetidin-2-one (3S,4R)-4-(Isobutenyloxy)-3-(triphenylmethylamino)azetidin-2-one (3S,4R)-4-Octyloxy-3-(trpipenylmethylamino)azetidin-2-one (3S,4R)-4-Phenoxy-3-(triphenylmethylamino)azetidin-2-one (3S,4S)-4-Phenoxy-3-(triphenylmethylamino)azetidin-2-one (3S,4R)-3-[[(4-Iodophenyl)diphenylmethyl]amino]-4-(isobutoxy)azetidin-2-one
(3S,4R)-4-[[2-(Pyrid-3-yl)-1,3-dithian-2-yl]methoxy]-3-(triphenylmethylamino)azetidin-2-one
(3S,4S)-4-(Prop-2-ynyloxy)-3-(triphenylmethylamino)azetidin-2-one
Methyl 4-[(3S,4S)-2-oxo-3-(triphenylmethylamino)azetidin-4-yloxy]but-2-ynoate
Methyl 4-[(3S,4R)-2-oxo-3-(triphenylmethylamino)azetidin-4-yloxy]but-2-ynoate
(3S,4R)-4-[(2(5H)Furanon-4-yl)methoxy]-3-(triphenylmethylamino)azetidin-2-one
(S)-3-(Triphenylmethylamino)azetidin-2-one
(RS)-3-(Triphenylmethylamino)azetidin-2-one
(3S,4S)-4-[3-(Methoxycarbonyl)propoxy]-3-(triphenylmethylamino)azetidin-2-one
(3R,4R)-4-(Methylsulfonyl)-3-(triphenylmethylamino)azetidin-2-one.

The following compound was found active at either increased uM or longer pretreatment time:
(3S,4S)-4-[3-(Methoxycarbonyl)propoxy]-3-(triphenylmethylamino)azetidin-2-one Apoptosis Assay:
Materials: Cotmpounds
Compounds were made as stocks (5–100 mM) in dimethylsulfoxide (DMSO) and diluted in DMSO to provide final concentrations, with DMSO concentrations ranging from 0.1–1%.

Preparation of cells
HL-60 cells were obtained from American Type Culture Collection and grown in RPMI-1640 media supplemented with 10% fetal bovine serum at 37°, 5% $CO_2$. Cells were seeded in T-flasks at 0.03 to $0.08 \times 10^6$ cells/ml and used for experiments at 0.5 to $0.6 \times 10^6$ cells/ml. Other proliferative cells can be used. In addition, leukemic cells can be isoloted from leukemic patients for ex vivo use.

Proliferation rind apoptosis
The functional status of cells was measured in one or more ways. First cell viability was assessed by the ability of the cells to exclude trypan blue stain.

A second, more sensitive and quantitative method was to measure DNA synthesis, using the incorporation of [$^3$H] thymidine into newly-formed DNA as the index of synthesis. In these assays, cells were treated with various concentrations of compounds or vehicle and kept in cell culture for different lengths of time (1 to 3 days). In a typical experiment, cells were then given a pulse of [$^3$H]thymidine (0.1–1 $\mu$Ci) then removed from culture 6–48 hours later, washed 2x with PBS and then treated with 0.2 N NaOH for 30 min followed by addition of 15% trichloroacetic acid for 2 hrs. The total sample from each well was filtered through GF/C Watman glass microfilters under vacuum and washed 3x with 5% trichloroacetic acid. The incorporation of [$^3$H] thymidine into DNA bound to the filter was determined using liquid scintillation spectroscopy.

Measurement of DNA fragmentation, determines not only the amount of cell death, but also provides insight into mechanism. When cells undergo programmed cell death or apoptosis, but not necrosis, cellular DNA is broken down into oligonucleosomal fragments which can be discerned on gels (Kerr et al., Cancer 73: 2013–2026, (1994)). Cells were treated for various times (3–24 hours) with different concentrations of compounds or vehicle. The washed cells were lysed by resuspending them in 200 $\mu$L of cold, sterile detergent buffer (10 mM Tris-HCl, pH 7.5, 1 mM EDTA, 0.2% Triton X-100) and incubated on ice 30 min. Cellular protein and RNA were enzymatically degraded by incubation with 75 $\mu$g/mL RNAse A for 1 hour at 37°, then 200 $\mu$g/mL Proteinase K and 0.5% SDS (final) for 1 hour at 37°. An internal standard of DNA was added during the cell lysis and its recovery used as a confirmation of efficient extraction of cellular DNA fragments. The samples were extracted twice with an equal volume of cold, buffer saturated phenol, once with phenol/chloroform/isoamyl alcohol (25:24:1. v/v), and once with chloroform. NaCl (300 mM final) and cold ethanol were added, the solution was vortexed and let stand overnight. The ethanol was removed and the samples and DNA bp standards (Sigma) were run on a 1% agarose gel with TBE buffer with ethidium bromide (45 mM Tris, pH 8.0, 45 mM boric acid, 1 mM EDTA). The DNA was visualized under UV light (UVP Gel Documentation system) and the size of DNA fragments noted by comparison to molecular weight standards.

Protein analysis
Protein concentrations were determined using the method of Bradford. M., Anal. Biochem. 72: 248–254, (1976), with reagents purchased from Bio-Rad (Hercules, Calif.).

Figure 3:
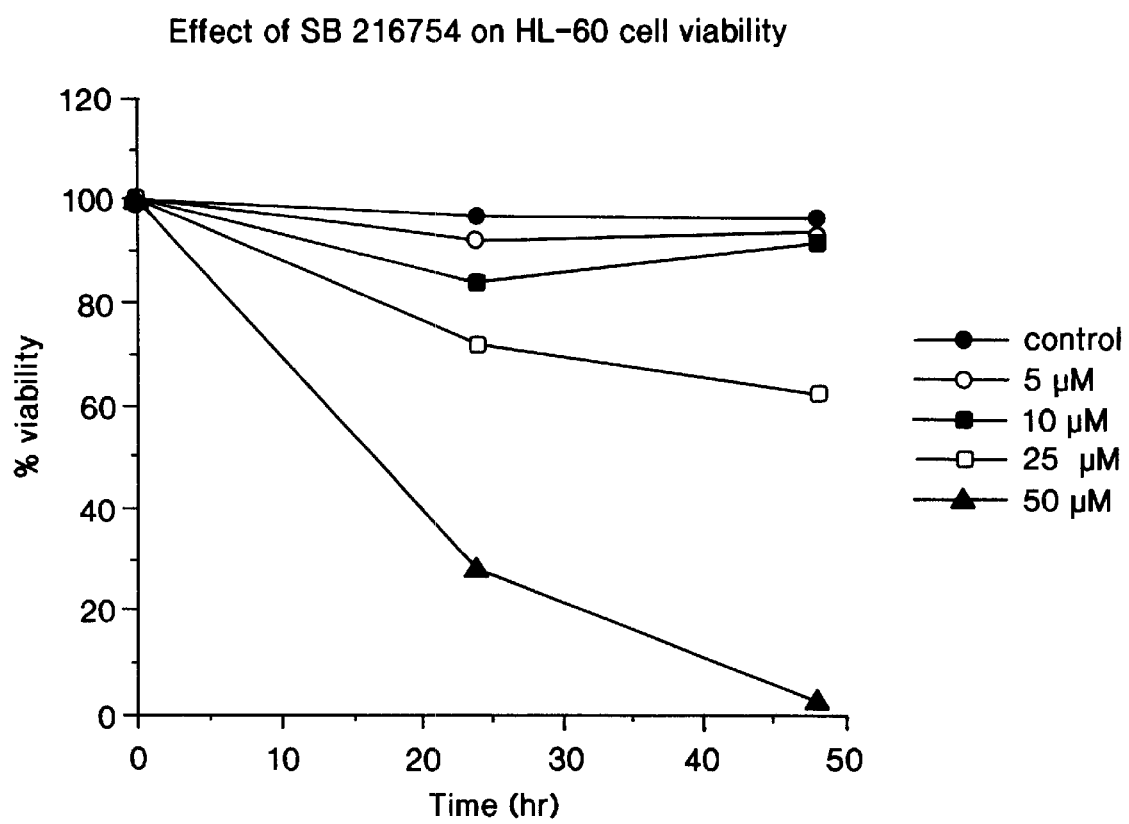
FIG. 3 demonstrates the ability of SB 216754, ((3S,4R)-4-(isobutenyloxy)-3-triphenylmethylamino)azetidin-2-one) to decrease viability of HL-60 cells.
Figure 4:
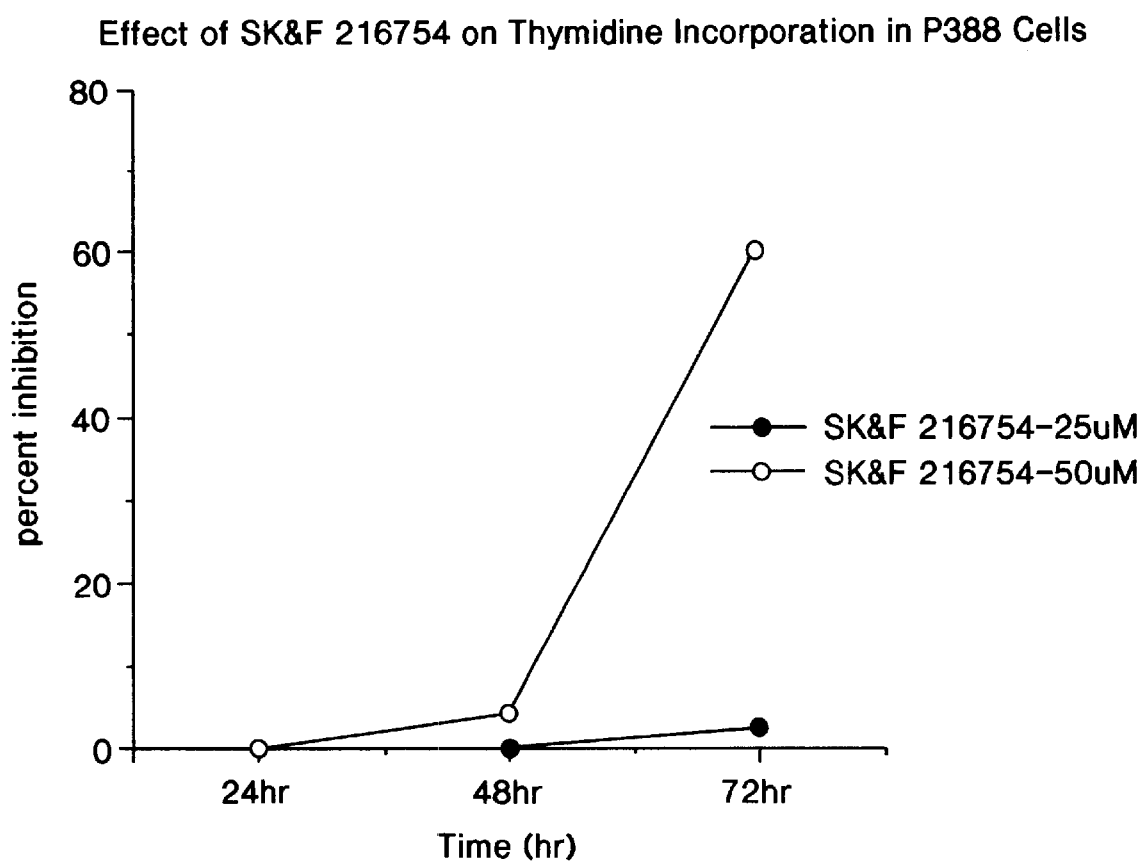
FIG. 4 demonstrates the ability of ((3S,4R)-4-(isobutenyloxy)-3-triphenylmethylamino)azetidin-2-one) to block the incorporation of thymidine into P388 cells.
Figure 5:
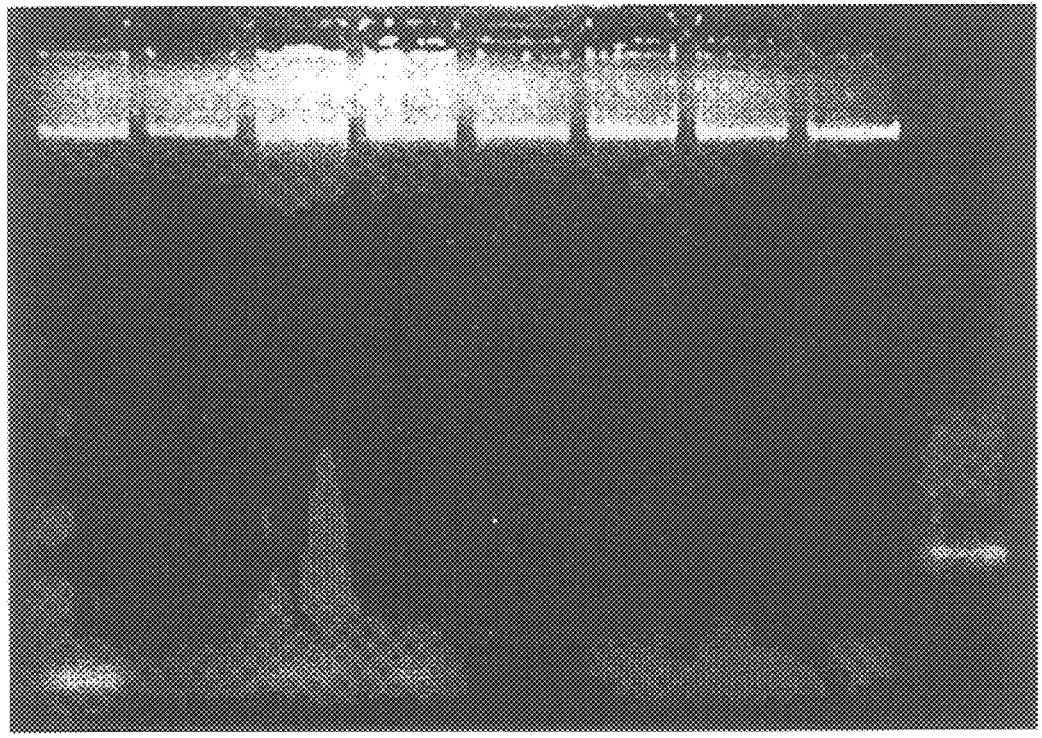
FIG. 5 demonstrates the ability of ((3S,4R)-4-(isobutenyloxy)-3-triphenylmethylamino)azetidin-2-one) to induce DNA fragmenatation in P388 cells.

Results
As mentioned in the "Background of the Invention", we have recently demonstrated that CoA-IT inhibitors block the proliferation and induce apoptosis of several neoplastic cell lines. Data below shows that compounds of formula I have the same effects. For example, FIG. 3 demonstrates that compounds of formula 1 cause a time and dose-dependent decrease in cell viability of cultured HL-60 cells. A concentration of 50 uM of Compound 1, Example 24, caused a 70% and 97% decrease in cell viability at 24 and 48 hr, respectively, after additions. The next studies were designed to determine if compounds of formula I would have similar effects on other neoplastic cells. Two other neoplastic cell types were examined. The first were P388 murine leukemia cells. These cells are utilized as a key test for antitumor activity by the National Cancer Institute in cancer chemotherapy screening studies. In P388 cells, we monitored the synthesis of new DNA by measuring thyrmidine incorporation into DNA as a measure of cell proliferation. Compound 1 caused a marked reduction (at 72 hr at 50 uM) in the capacity of these cells to incorporate thymidine into newly-formed DNA (FIG. 4). A major mechanism that blocks cell proliferation and reduces cell numbers is the induction of apoptosis. Apoptosis was determined in these studies by examining internucleosomal DNA fragmentation. Compound 1 induced apoptosis of P388 cells as determined by the marked appearance of internucleosomal DNA fragments (DNA ladders) after addition of compound (FIG. 5).

Figure 6:
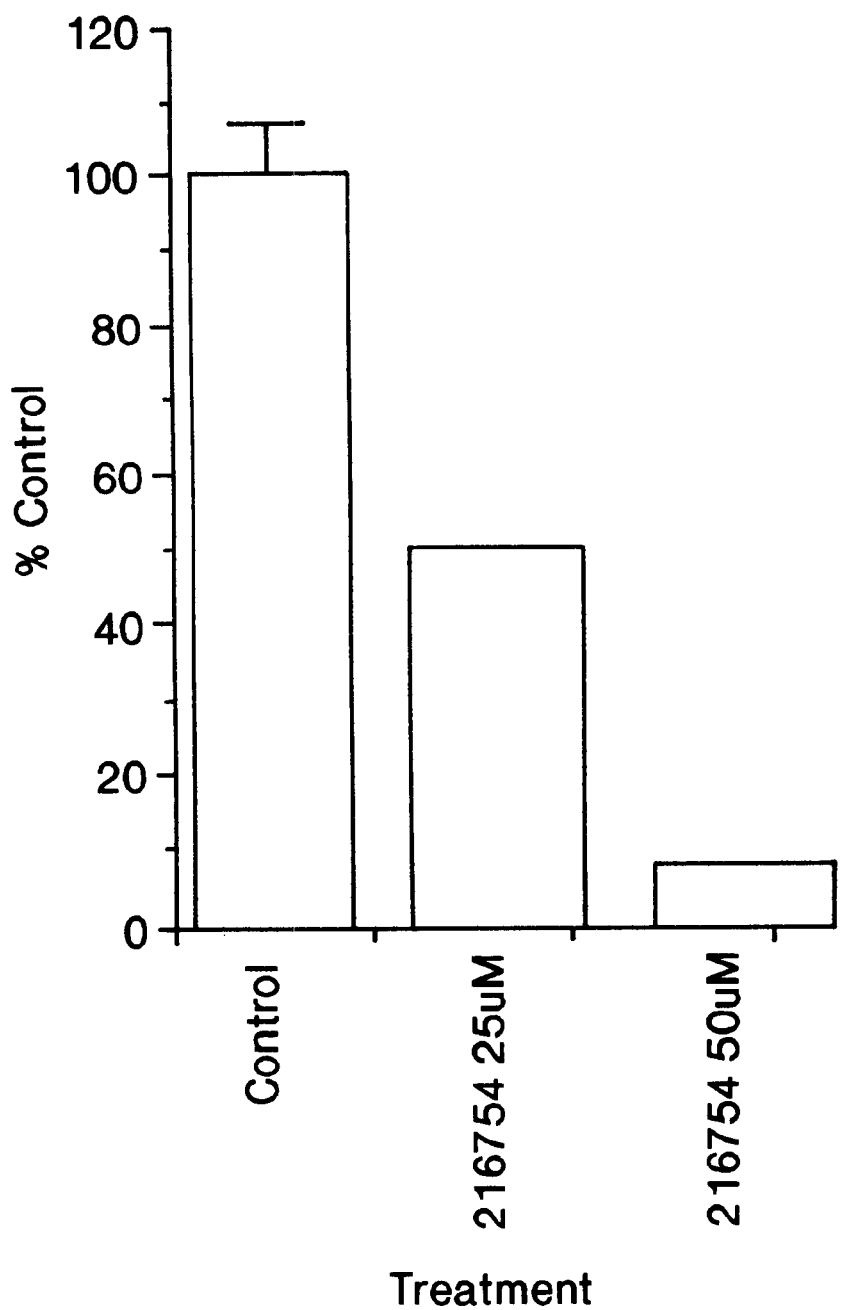
FIG. 6 demonstrates the ability of ((3S,4R)-4-(isobutenyloxy)-3-triphenylmethylamino)azetidin-2-one) to block the incorporation of thymidine into chronic myclogenous leukemia cells.
Figure 7:
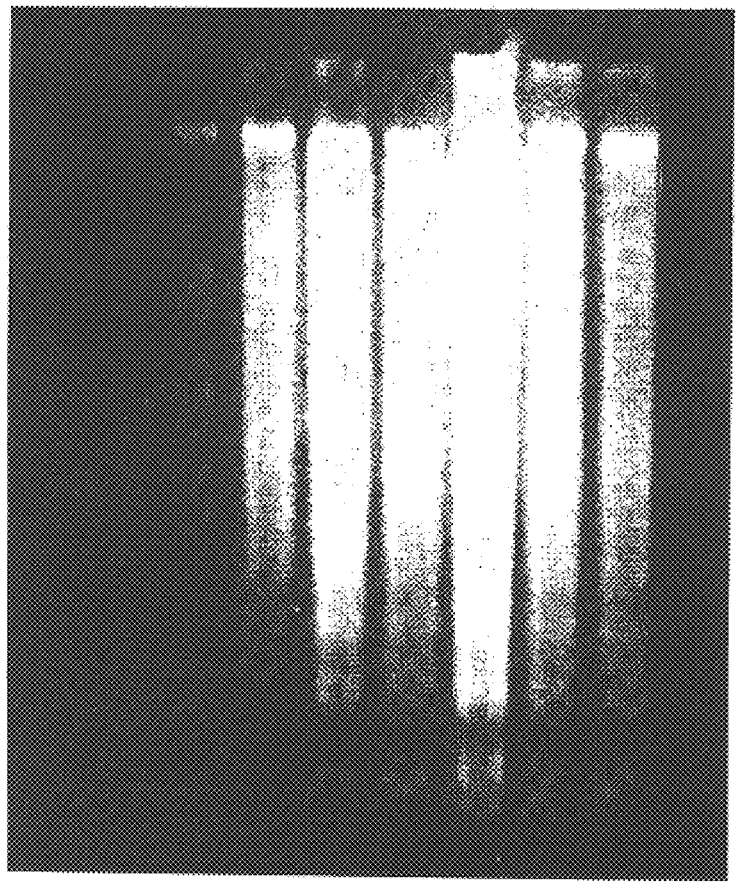
FIG. 7 demonstrates the ability of ((3S,4R)-4-(isobutenyloxy)-3-triphenylmethylamino)azetidin-2-one) to induce DNA fragmenatation in chronic myelogenous leukemia cells.

Finally, Compound 1 was examined for its capacity to influence new DNA synthesis and DNA fragmentation in cells from patients with acute myelogenous leukemia (AML). FIG. 6 shows that Compound 1 prevented thymidine incorporation into AML cells. At similar concentrations and time points, this compound caused DNA "ladder" formation in AML cells from patients (FIG. 7). Taken together these data reveal that compounds of formula I inhibit cell proliferation and induce apoptosis of a variety of neoplastic cells. Moreover, these studies point out the utility of these compounds as chemotherapeutic agents in proliferative disorders.

As used herein, various abbreviations and explanations are as follows: [$^3$H], a molecule that contains tritium atoms, a radioactive isotope; A23187, a compound that allows free entry of calcium into a cell; AA, arachidonic acid, 5-8-11-14 eicosatetraenoic acid; arachidonate, arachidonic acid contained within a phospholipid; free arachidonic acid, arachidonic acid that is not contained within a phospholipid;

[²H₈]arachidonic acid, the form of arachidonic acid labeled with 8 deuterium atoms, a stable isotope; 1-alkyl, 1-O-alkyl; 1-alkenyl, 1-O-alk-1'-enyl; BSA, bovine serum albumin; CoA, coenzyme A; CoA-IT. CoA-independent transacylase; COX, cyclooxygenase; DTT, dithiothreitol; EGTA, [ethylenebis(oxyethylenenitrilo)]tetra acetic acid, a calcium chelator; GPC, sn-glycero-3-phosphocholine; EDTA, a metal ion chelator; GPE, sn-glycero-3-phosphoethanolamine; GC/MS, gas chromatography and mass spectrometry; 5HETE, 5(S)-hydroxyeicosa-6,8,11,14-tetraenoic acid; 15HETE, 15(S)-hydroxyeicosa-5,8,11,13-tetraenoic acid; HL-60, American Type Tissue Culture designated cell line similar to a monocyte; 5LO, 5-lipoxygenase; LTB$_4$, leukotriene B$_4$; LTC$_4$, leukotriene C$_4$; LTD$_4$, leukotriene D$_4$; lyso PAF, 1-alkyl-2-lyso-GPC, lyso platelet-activating factor; PLA$_2$, phospholipase A$_2$; PBS, phosphate buffered saline; PAF, platelet activating factor, 1-alkyl-2-acetyl-GPC; PL, phospholipid; PC, phosphatidylcholine; PE, phosphatidylethanolamine, PI, phosphatidylinositol; PMN, polymorphonuclear neutrophilic cell, neutrophil; PS phosphatidylserine; Rf, the distance a compound travels as a fraction of the solvent front; TLC, thin layer chromatography; U937, American Type Tissue Culture designated cell line similar to a monocyte.

All publications, including but not limited to patents and patent applications, cited in this specification are herein incorporated by reference as if each individual publication were specifically and individually indicated to be incorporated by reference herein as though fully set forth.

The above description fully discloses the invention including preferred embodiments thereof. Modifications and improvements of the embodiments specifically disclosed herein are within the scope of the following claims. Without further elaboration, it is believed that one skilled in the art can, using the preceding description, utilize the present invention to its fullest extent. Therefore, the Examples herein are to be construed as merely illustrative and not a limitation of the scope of the present invention in any way. The embodiments of the invention in which an exclusive property or privilege is claimed are defined as follows.

What is claimed is:

1. A method of inhibiting or reducing cell proliferation in a human or mammal, in need of such treatment, which method comprises administering to said human or mammal an effective CoA-independent transacylase (CoA-IT) inhibiting amount of a compound of the formula:

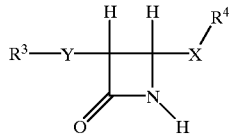

wherein

Y is NH;

X is O or S(O)m;

m is 0 or an integer having a value of 1, or 2;

$R_3$ is optionally substituted triphenylmethyl;

$R_4$ is optionally substituted $C_{1-10}$ alkyl, $(CR_{10}R_{20})n$—C≡C—$R_5$, or $(CR_{10}R_{20})_nC(R_{10})$=$C(R_7)_2$;

n is an integer having a value of 1 to 4;

$R_{10}$ and $R_{20}$ are independently hydrogen or $C_{1-4}$ alkyl;

$R_5$ is hydrogen, alkyl, aryl, arylalkyl, heteroaryl, heteroarylalkyl, $C(O)_2R_6$, or $C(O)R_6$, wherein the alkyl, aryl, arylalkyl, heteroaryl, or heteroarylalkyl moieties may be optionally substituted;

$R_6$ is $C_{1-10}$ alkyl, aryl, arylalkyl, heteroaryl, heteroarylalkyl, heterocyclic, or heterocyclicalkyl, wherein the alkyl, aryl, arylalkyl, heteroaryl, heteroarylalkyl, heterocyclic, or heterocyclicalkyl moieties may be optionally substituted;

$R_7$ is independently hydrogen, $C_{1-10}$ alkyl, aryl, arylalkyl, heteroaryl, heteroarylalkyl, heterocyclic, or heterocyclicalkyl, wherein the alkyl, aryl, arylalkyl, heteroaryl, heteroarylalkyl, heterocyclic, or heterocyclicalkyl moieties may be optionally substituted;

or a pharmaceutically acceptable salt thereof.

2. The method according to claim 1 wherein the CoA-IT inhibitor is co-administered with an effective amount of ET-18-O-CH$_3$ or an alkyl lysophospholipid analog, or other anti-proliferative or chemotherapeutic agent.

3. The method according to claim 1 wherein the mammal is afflicted with psoriasis, rheumatoid arthritis, or atherosclerosis, or other disease characterized by abnormal cell proliferation.

4. A method of treating a cancerous cell growth in a mammal, in need of such treatment, which method comprises administering to said mammal an effective amount of a compound of the formula:

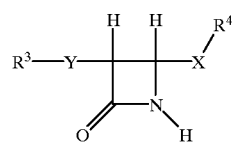

wherein

Y is NH;

X is O or S(O)m;

m is 0 or an integer having a value of 1, or 2;

$R_3$ is optionally substituted triphenylmethyl;

$R_4$ is optionally substituted $C_{1-10}$ alkyl, $(CR_{10}R_{20})n$—C≡C—$R_5$, or $(CR_{10}R_{20})_nC(R_{10})$=$C(R_7)_2$;

n is an integer having a value of 1to 4;

$R_{10}$ and $R_{20}$ are independently hydrogen or $C_{1-4}$ alkyl;

$R_5$ is hydrogen, alkyl, aryl, arylalkyl, heteroaryl, heteroarylalkyl, $C(O)_2R_6$, or $C(O)R_6$, wherein the alkyl, aryl, arylalkyl, heteroaryl, or heteroarylalkyl moieties may be optionally substituted;

$R_6$ is $C_{1-10}$ alkyl, aryl, arylalkyl, heteroaryl, heteroarylalkyl, heterocyclic, or heterocyclicalkyl, wherein the alkyl, aryl, arylalkyl, heteroaryl, heteroarylalkyl, heterocyclic, or heterocyclicalkyl moieties may be optionally substituted;

$R_7$ is independently hydrogen, $C_{1-10}$ alkyl, aryl, arylalkyl, heteroaryl, heteroarylalkyl, heterocyclic, or heterocyclicalkyl, wherein the alkyl, aryl, arylalkyl, heteroaryl, heteroarylalkyl, heterocyclic, or heterocyclicalkyl moieties may be optionally substituted;

or a pharmaceutically acceptable salt thereof.

5. The method according to claim 4 wherein the inhibitor is co-administered with an effective amount of ET-18-O-CH$_3$ or an alkyl lysophospholipid analog or an alkyl lysophospholipid analog, or other anti-proliferative or chemotherapeutic agent.

6. The method according to claim 4 wherein the mammal is afflicted with leukemia, or other cancers.

7. A method of inducing apoptosis in a human or mammal, in need of such treatment which method comprises administering to said human or mammal an effective CoA-independent transacylase (CoA-IT) inhibiting amount of a compound of the formula:

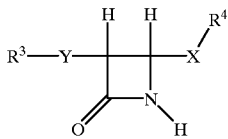

wherein
Y is NH;
X is O or S(O)m;
m is 0 or an integer having a value of 1, or 2;
$R_3$ is optionally substituted triphenylmethyl;
$R_4$ is optionally substituted $C_{1-10}$ alkyl, $(CR_{10}R_{20})n—C\equiv C—R_5$, or $(CR_{10}R_{20})_nC(R_{10})=C(R_7)_2$;
n is an integer having a value of 1 to 4;
$R_{10}$ and $R_{20}$ are independently hydrogen or $C_{1-4}$ alkyl;
$R_5$ is hydrogen, alkyl, aryl, arylalkyl, heteroaryl, heteroarylalkyl, $C(O)_2R_6$, or $C(O)R_6$, wherein the alkyl, aryl, arylalkyl, heteroaryl, or heteroarylalkyl moieties may be optionally substituted;
$R_6$ is $C_{1-10}$ alkyl, aryl, arylalkyl, heteroaryl, heteroarylalkyl, heterocyclic, or heterocyclicalkyl, wherein the alkyl, aryl, arylalkyl, heteroaryl, heteroarylalkyl, heterocyclic, or heterocyclicalkyl moieties may be optionally substituted;
$R_7$ is independently hydrogen, $C_{1-10}$ alkyl, aryl, arylalkyl, heteroaryl, heteroarylalkyl, heterocyclic, or heterocyclicalkyl, wherein the alkyl, aryl, arylalkyl, heteroaryl, heteroarylalkyl, heterocyclic, or heterocyclicalkyl moieties may be optionally substituted;
or a pharmaceutically acceptable salt thereof.

8. The method according to claim 7 wherein the inhibitor is co-administered with an effective amount of ET-18—O—CH$_3$ or an alkyl lysophospholipid analog or an alkyl lysophospholipid analog, or other anti-proliferative or chemotherapeutic agent.

9. The method according to claim 1 wherein X is oxygen.

10. The method according to claim 1 wherein X is S(O)m.

11. The method according to claim 1 wherein $R_4$ is an optionally substituted $C_{1-10}$ alkyl.

12. The method according to claim 1 wherein $R_4$ is $(CR_{10}R_{20})n—c\equiv c—R_5$.

13. The method according to claim 1 wherein $R_4$ is $(CR_{10}R_{20})_nC(R_{10})=C(R_7)_2$.

14. The method according to claim 1 wherein the compound is (3RS,4RS)-4-(Isobutoxy)-3-(triphenylmethylamino)azetidin-2-one (3R,4R)-4-(Isobutoxy)-3-(triphenylmethylamino)azetidin-2-one (3S,4S)-4-(Isobutoxy)-3-(triphenylmethylamino)azetidin-2-one (3R,4R)-4-(Isobutylthio)-3-(triphenylmethylamino)azetidin-2-one (3R,4R)-4-(Isobutylsulfonyl)-3-(triphenylmethylamino)azetidin-2-one (3S,4R)-4-(Isobutoxy)-3-(triphenylmethylamino)azetidin-2-one (3S,4R)-4-(Propoxy)-3-(triphenylmethylamino)azetidin-2-one (3S,4S)-4-(Propoxy)-3-(triphenylmethylamino)azetidin-2-one (3S,4R)-4-(Benzyloxy)-3-(triphenylmethylamino)azetidin-2-one (3S,4S)-4-(Benzyloxy)-3-(triphenylmethylamino)azetidin-2-one (3S,4R)-4-Methoxy-3-(triphenylmethylamino)azetidin-2-one (3S,4R)-4-(Isobutenyloxy)-3-(triphenylmethylamino)azetidin-2-one (3S,4R)-4-Octyloxy-3-(triphenylmethylamino)azetidin-2-one (3S,4R)-4-Phenoxy-3-(triphenylmethylamino)azetidin-2-one (3S,4S)-4-Phenoxy-3-(triphenylmethylamino)azetidin-2-one (3S,4R)-3-[[(4-Iodophenyl)diphenylmethyl]amino]-4-(isobutoxy)azetidin-2-one (3S,4S)-4-[3-(Methoxycarbonyl)propoxy]-3-(triphenylmethylamino)azetidin-2-one (3S,4R)-4-[[2-(3-Pyridylmethyl)-1,3-dithian-2-yl]methoxy]-3-(triphenylmethylamino)azetidin-2-one (3S,4S)-4-(Prop-2-ynyloxy)-3-(triphenylmethylamino)azetidin-2-one Methyl 4-[(3S,4S)-2-oxo-3-(triphenylmethylamino)azetidin-4-yloxy]but-2-ynoate Methyl 4-[(3S,4R)-2-oxo-3-(triphenylmethylamino)azetidin-4-yloxy]but-2-ynoate (3S,4R)-4-(Isobutenyloxy-3-(triphenylmethylamino)azetidin-2-one 15. The method according to claim 4 wherein X is oxygen.

16. The method according to claim 4 wherein X is S(O)m.

17. The method according to claim 4 wherein $R_4$ is an optionally substituted $C_{1-10}$ alkyl.

18. The method according to claim 4 wherein $R_4$ is $(CR_{10}R_{20})n—c\equiv c—R_5$.

19. The method according to claim 4 wherein $R_4$ is $(CR_{10}R_{20})_nC(R_{10})=C(R_7)_2$.

20. The method according to claim 4 wherein the compound is (3RS,4RS)-4-(Isobutoxy)-3-(triphenylmethylamino)azetidin-2-one (3R,4R)-4-(Isobutoxy)-3-(triphenylmethylamino)azetidin-2-one (3S,4S)-4-(Isobutoxy)-3-(triphenylmethylamino)azetidin-2-one (3R,4R)-4-(Isobutylthio)-3-(triphenylmethylamino)azetidin-2-one (3R,4R)-4-(Isobutysulfonyl)-3-(triphenylmethylamino)azetidin-2-one (3S,4R)-4-(Isobutoxy)-3-(triphenylmethylamino)azetidin-2-one (3S,4R)-4-(Propoxy)-3-(triphenylmethylamino)azetidin-2-one (3S,4S)-4-(Propoxy)-3-(triphenylmethylamino)azetidin-2-one (3S,4R)-4-(Benzyloxy)-3-(triphenylmethylamino)azetidin-2-one (3S,4S)-4-(Benzyloxy)-3-(triphenylmethylamino)azetidin-2-one (3S,4R)-4-Methoxy-3-(triphenylmethylamino)azetidin-2-one (3S,4R)-4-(Isobutenyloxy)-3-(triphenylmethylamino)azetidin-2-one (3S,4R)-4-Octyloxy-3-(triphenylmethylamino)azetidin-2-one (3S,4R)-4-Phenoxy-3-(triphenylmethylamino)azetidin-2-one (3S,4S)-4-Phenoxy-3-(triphenylmethylamino)azetidin-2-one (3S,4R)-3-[[(4-Iodophenyl)diphenylmethyl]amino]-4-(isobutoxy)azetidin-2-one (3S,4S)-4-[3-(Methoxycarbonyl)propoxy]-3-(triphenylmethylamino)azetidin-2-one (3S,4R)-4-[[2-(3-Pyridylmethyl)-1,3-dithian-2-yl]methoxyl]-3-(triphenylmethylamino)azetidin-2-one (3S,4S)-4-(Prop-2-ynyloxy)-3-(triphenylmethylamino)azetidin-2-one Methyl 4-[(3S,4S)-2-oxo-3-(triphenylmethylamino)azetidin-4yloxy]but-2-ynoate Methyl 4-[(3S,4R)-2-oxo-3-(triphenylmethylamino)azetidin-4yloxy]but-2-ynoate (3S,4R)-4-(Isobutenyloxy)-3-(triphenylmethylamino)azetidin-2-one 21. The method according to claim 7 wherein X is oxygen.

22. The method according to claim 7 wherein X is S(O)m.

23. The method according to claim 7 wherein $R_4$ is an optionally substituted $C_{1-10}$ alkyl.

24. The method according to claim 7 wherein $R_4$ is $(CR_{10}R_{20})n$—c≡c—$R_5$.

25. The method according to claim 7 wherein $R_4$ is $(CR_{10}R_{20})_nC(R_{10})=C(R_7)_2$.

26. The method according to claim 7 wherein the compound is (3RS,4RS)-4-(Isobutoxy)-3-(triphenylmethylamino)azetidin-2-one (3R,4R)-4-(Isobutoxy)-3-(triphenylmethylamino)azetidin-2-one (3S,4S)-4-(Isobutoxy)-3-(triphenylmethylamino)azetidin-2-one (3R,4R)-4-(Isobutylthio)-3-(triphenylmethylamino)azetidin-2-one (3R,4R)-4-(Isobutylsulfonyl)-3-(triphenylmethylamino)azetidin-2-one (3S,4R)-4-(Isobutoxy)-3-(triphenylmethylamino)azetidin-2-one (3S,4R)-4-(Propoxy)-3-(triphenylmethylamino)azetidin-2-one (3S,4S)-4-(Propoxy)-3-(triphenylmethylamino)azetidin-2-one (3S,4R)-4-(Benzyloxy)-3-(triphenylmethylamino)azetidin-2-one (3S,4S)-4-(Benzyloxy)-3-(triphenylmethylamino)azetidin-2-one (3S,4R)-4-Methoxy-3-(triphenylmethylamino)azetidin-2-one (3S,4R)-4-(Isobutenyloxy)-3-(triphenylmethylamino)azetidin-2-one (3S,4R)-4-Octyloxy-3-(triphenylmethylamino)azetidin-2-one (3S,4R)-4-Phenoxy-3-(triphenylmethylamino)azetidin-2-one (3S,4S)-4-Phenoxy-3-(triphenylmethylamino)azetidin-2-one (3S,4R)-3-[[(4-Iodophenyl)diphenylmethyl]amino]-4-(isobutoxy)azetidin-2-one (3S,4S)-4-[3-(Methoxycarbonyl)propoxy]-3-(triphenylmethylamino)azetidin-2-one (3S,4R)-4-[[2-(3-Pyridylmethyl)-1,3-dithian-2-yl]methoxy]-3-(triphenylmethylamino)azetidin-2-one (3S,4S)-4-(Prop-2-ynyloxy)-3-(triphenylmethylamino)azetidin-2-one Methyl 4-[(3S,4S)-2-oxo-3-(triphenylmethylamino)azetidin-4-yloxy]but-2-ynoate Methyl 4-[(3S,4R)-2-oxo-3-(triphenylmethylamino)azetidin-4-yloxy]but-2-ynoate (3S,4R)-4-(Isobutenyloxy)-3-(triphenylmethylamino)azetidin-2-one 27. The method of inhibiting of reducing cell proliferation in a mammal in need of such treatment which comprises administering to said mammal an effective CoA-independent transacylase (CoA-IT) inhibiting amount of (3S,4R)-4-[(2(5H)Furanon-4-yl)methoxy]-3-(triphenylmethylamino)azetidin-2-one;

(S)-3-(Triphenylmethylamino)azetidin-2-one; or (RS)-3-(Triphenylmethylamino)azetidin-2-one.

28. The method of inducing apoptosis in a mammal in need of such treatment, which method comprises administering to said mammal an effective effective CoA-independent transacylase (CoA-IT) inhibiting amount of (3S,4R)-4-[(2(5H)Furanon-4-yl)methoxy]-3-(triphenylmethylamino)azetidin-2-one;

(S)-3-(Triphenylmethylamino)azetidin-2-one; or (RS)-3-(Triphenylmethylamino)azetidin-2-one.

* * * * *